(12) United States Patent
Budiman

(10) Patent No.: US 12,171,548 B2
(45) Date of Patent: *Dec. 24, 2024

(54) MULTI-RATE ANALYTE SENSOR DATA COLLECTION WITH SAMPLE RATE CONFIGURABLE SIGNAL PROCESSING

(71) Applicant: ABBOTT DIABETES CARE INC., Alameda, CA (US)

(72) Inventor: Erwin Satrya Budiman, Fremont, CA (US)

(73) Assignee: ABBOTT DIABETES CARE INC., Alameda, CA (US)

( * ) Notice: Subject to any disclaimer, the term of this patent is extended or adjusted under 35 U.S.C. 154(b) by 185 days.

This patent is subject to a terminal disclaimer.

(21) Appl. No.: 17/098,286

(22) Filed: Nov. 13, 2020

(65) Prior Publication Data

US 2021/0076994 A1 Mar. 18, 2021

Related U.S. Application Data

(63) Continuation of application No. 15/292,107, filed on Oct. 12, 2016, now Pat. No. 10,874,336, which is a continuation of application No. 14/210,330, filed on Mar. 13, 2014, now Pat. No. 9,474,475.

(60) Provisional application No. 61/800,878, filed on Mar. 15, 2013.

(51) Int. Cl.
*A61B 5/145* (2006.01)
*A61B 5/00* (2006.01)
*G16H 10/60* (2018.01)

(52) U.S. Cl.
CPC ............ *A61B 5/14532* (2013.01); *A61B 5/72* (2013.01); *A61B 5/7225* (2013.01); *A61B 5/725* (2013.01); *A61B 5/742* (2013.01); *A61B 2562/0295* (2013.01); *G16H 10/60* (2018.01)

(58) Field of Classification Search
CPC .............. A61B 5/1455; A61B 5/14551; A61B 5/14552; A61B 5/72

See application file for complete search history.

(56) References Cited

U.S. PATENT DOCUMENTS

| | | |
|---|---|---|
| 3,581,062 A | 5/1971 | Aston |
| 3,926,760 A | 12/1975 | Allen et al. |
| 3,949,388 A | 4/1976 | Fuller |

(Continued)

FOREIGN PATENT DOCUMENTS

| | | |
|---|---|---|
| DE | 202015010002 U1 | 12/2022 |
| EP | 0098592 | 1/1984 |

(Continued)

OTHER PUBLICATIONS

U.S. Appl. No. 15/292,107 (US 2017/0027483), Oct. 12, 2016 (Feb. 2, 2017).

(Continued)

*Primary Examiner* — Eric F Winakur
(74) *Attorney, Agent, or Firm* — Baker Botts L.L.P.

(57) ABSTRACT

Systems, methods and apparatus are provided for determining an estimate of an analyte level over time. The invention includes sampling sensor data using an analyte sensor positioned at least partially subcutaneously; storing a plurality of datasets of sensor data, each at a different rate; determining an estimated analyte level based on the datasets; and outputting the estimated analyte level to a display. Numerous additional aspects are disclosed.

18 Claims, 5 Drawing Sheets

(56) References Cited

U.S. PATENT DOCUMENTS

| | | |
|---|---|---|
| 3,960,497 A | 6/1976 | Acord et al. |
| 3,978,856 A | 9/1976 | Michel |
| 4,036,749 A | 7/1977 | Anderson |
| 4,055,175 A | 10/1977 | Clemens et al. |
| 4,129,128 A | 12/1978 | McFarlane |
| 4,245,634 A | 1/1981 | Albisser et al. |
| 4,327,725 A | 5/1982 | Cortese et al. |
| 4,344,438 A | 8/1982 | Schultz |
| 4,349,728 A | 9/1982 | Phillips et al. |
| 4,373,527 A | 2/1983 | Fischell |
| 4,392,849 A | 7/1983 | Petre et al. |
| 4,425,920 A | 1/1984 | Bourland et al. |
| 4,441,968 A | 4/1984 | Emmer et al. |
| 4,462,048 A | 7/1984 | Ross |
| 4,478,976 A | 10/1984 | Goertz et al. |
| 4,494,950 A | 1/1985 | Fischell |
| 4,509,531 A | 4/1985 | Ward |
| 4,527,240 A | 7/1985 | Kvitash |
| 4,538,616 A | 9/1985 | Rogoff |
| 4,545,382 A | 10/1985 | Higgins et al. |
| 4,619,793 A | 10/1986 | Lee |
| 4,671,288 A | 6/1987 | Gough |
| 4,703,756 A | 11/1987 | Gough et al. |
| 4,711,245 A | 12/1987 | Higgins et al. |
| 4,731,051 A | 3/1988 | Fischell |
| 4,731,726 A | 3/1988 | Allen, III |
| 4,749,985 A | 6/1988 | Corsberg |
| 4,757,022 A | 7/1988 | Shults et al. |
| 4,759,366 A | 7/1988 | Callaghan |
| 4,777,953 A | 10/1988 | Ash et al. |
| 4,779,618 A | 10/1988 | Mund et al. |
| 4,854,322 A | 8/1989 | Ash et al. |
| 4,871,351 A | 10/1989 | Feingold |
| 4,890,620 A | 1/1990 | Gough |
| 4,925,268 A | 5/1990 | Iyer et al. |
| 4,947,845 A | 8/1990 | Davis |
| 4,953,552 A | 9/1990 | DeMarzo |
| 4,986,271 A | 1/1991 | Wilkins |
| 4,995,402 A | 2/1991 | Smith et al. |
| 5,000,180 A | 3/1991 | Kuypers et al. |
| 5,002,054 A | 3/1991 | Ash et al. |
| 5,019,974 A | 5/1991 | Beckers |
| 5,050,612 A | 9/1991 | Matsumura |
| 5,055,171 A | 10/1991 | Peck |
| 5,068,536 A | 11/1991 | Rosenthal |
| 5,077,476 A | 12/1991 | Rosenthal |
| 5,082,550 A | 1/1992 | Rishpon et al. |
| 5,106,365 A | 4/1992 | Hernandez |
| 5,113,869 A | 5/1992 | Nappholz et al. |
| 5,122,925 A | 6/1992 | Inpyn |
| 5,135,004 A | 8/1992 | Adams et al. |
| 5,148,812 A | 9/1992 | Verrier et al. |
| 5,165,407 A | 11/1992 | Wilson et al. |
| 5,199,428 A | 4/1993 | Obel et al. |
| 5,202,261 A | 4/1993 | Musho et al. |
| 5,203,326 A | 4/1993 | Collins |
| 5,204,264 A | 4/1993 | Kaminer et al. |
| 5,210,778 A | 5/1993 | Massart |
| 5,231,988 A | 8/1993 | Wernicke et al. |
| 5,246,867 A | 9/1993 | Lakowicz et al. |
| 5,262,035 A | 11/1993 | Gregg et al. |
| 5,262,305 A | 11/1993 | Heller et al. |
| 5,264,104 A | 11/1993 | Gregg et al. |
| 5,264,105 A | 11/1993 | Gregg et al. |
| 5,279,294 A | 1/1994 | Anderson et al. |
| 5,285,792 A | 2/1994 | Sjoquist et al. |
| 5,293,877 A | 3/1994 | O'Hara et al. |
| 5,299,571 A | 4/1994 | Mastrototaro |
| 5,313,953 A | 5/1994 | Yomtov et al. |
| 5,320,715 A | 6/1994 | Berg |
| 5,320,725 A | 6/1994 | Gregg et al. |
| 5,322,063 A | 6/1994 | Allen et al. |
| 5,328,460 A | 7/1994 | Lord et al. |
| 5,330,634 A | 7/1994 | Wong et al. |
| 5,340,722 A | 8/1994 | Wolfbeis et al. |
| 5,342,789 A | 8/1994 | Chick et al. |
| 5,356,786 A | 10/1994 | Heller et al. |
| 5,360,404 A | 11/1994 | Novacek et al. |
| 5,365,426 A | 11/1994 | Siegel et al. |
| 5,372,427 A | 12/1994 | Padovani et al. |
| 5,376,070 A | 12/1994 | Purvis et al. |
| 5,379,238 A | 1/1995 | Stark |
| 5,384,547 A | 1/1995 | Lynk et al. |
| 5,390,671 A | 2/1995 | Lord et al. |
| 5,391,250 A | 2/1995 | Cheney, II et al. |
| 5,400,795 A | 3/1995 | Murphy et al. |
| 5,408,999 A | 4/1995 | Singh et al. |
| 5,411,647 A | 5/1995 | Johnson et al. |
| 5,425,749 A | 6/1995 | Adams |
| 5,425,868 A | 6/1995 | Pedersen |
| 5,431,160 A | 7/1995 | Wilkins |
| 5,431,921 A | 7/1995 | Thombre |
| 5,438,983 A | 8/1995 | Falcone |
| 5,462,645 A | 10/1995 | Albery et al. |
| 5,472,317 A | 12/1995 | Field et al. |
| 5,482,473 A | 1/1996 | Lord et al. |
| 5,489,414 A | 2/1996 | Schreiber et al. |
| 5,497,772 A | 3/1996 | Schulman et al. |
| 5,505,828 A | 4/1996 | Wong et al. |
| 5,507,288 A | 4/1996 | Bocker et al. |
| 5,509,410 A | 4/1996 | Hill et al. |
| 5,514,718 A | 5/1996 | Lewis et al. |
| 5,520,191 A | 5/1996 | Karlsson et al. |
| 5,531,878 A | 7/1996 | Vadgama et al. |
| 5,532,686 A | 7/1996 | Urbas et al. |
| 5,543,326 A | 8/1996 | Heller et al. |
| 5,552,997 A | 9/1996 | Massart |
| 5,568,400 A | 10/1996 | Stark et al. |
| 5,568,806 A | 10/1996 | Cheney, II et al. |
| 5,569,186 A | 10/1996 | Lord et al. |
| 5,582,184 A | 12/1996 | Erickson et al. |
| 5,586,553 A | 12/1996 | Halili et al. |
| 5,593,852 A | 1/1997 | Heller et al. |
| 5,601,435 A | 2/1997 | Quy |
| 5,609,575 A | 3/1997 | Larson et al. |
| 5,628,310 A | 5/1997 | Rao et al. |
| 5,628,890 A | 5/1997 | Carter et al. |
| 5,634,468 A | 6/1997 | Platt et al. |
| 5,640,954 A | 6/1997 | Pfeiffer et al. |
| 5,653,239 A | 8/1997 | Pompei et al. |
| 5,660,163 A | 8/1997 | Schulman et al. |
| 5,665,222 A | 9/1997 | Heller et al. |
| 5,707,502 A | 1/1998 | McCaffrey et al. |
| 5,711,001 A | 1/1998 | Bussan et al. |
| 5,711,861 A | 1/1998 | Ward et al. |
| 5,720,295 A | 2/1998 | Greenhut et al. |
| 5,724,030 A | 3/1998 | Urbas et al. |
| 5,733,259 A | 3/1998 | Valcke et al. |
| 5,735,285 A | 4/1998 | Albert et al. |
| 5,741,211 A | 4/1998 | Renirie et al. |
| 5,749,907 A | 5/1998 | Mann |
| 5,772,586 A | 6/1998 | Heinonen et al. |
| 5,785,660 A | 7/1998 | van Lake et al. |
| 5,791,344 A | 8/1998 | Schulman et al. |
| 5,792,065 A | 8/1998 | Xue et al. |
| 5,804,047 A | 9/1998 | Karube et al. |
| 5,820,551 A | 10/1998 | Hill et al. |
| 5,822,715 A | 10/1998 | Worthington et al. |
| 5,891,047 A | 4/1999 | Lander et al. |
| 5,891,049 A | 4/1999 | Cyrus et al. |
| 5,899,855 A | 5/1999 | Brown |
| 5,914,026 A | 6/1999 | Blubaugh, Jr. et al. |
| 5,918,603 A | 7/1999 | Brown |
| 5,925,021 A | 7/1999 | Castellano et al. |
| 5,935,224 A | 8/1999 | Svancarek et al. |
| 5,942,979 A | 8/1999 | Luppino |
| 5,951,485 A | 9/1999 | Cyrus et al. |
| 5,957,854 A | 9/1999 | Besson et al. |
| 5,960,797 A | 10/1999 | Kramer et al. |
| 5,961,451 A | 10/1999 | Reber et al. |
| 5,964,993 A | 10/1999 | Blubaugh, Jr. et al. |
| 5,965,380 A | 10/1999 | Heller et al. |
| 5,971,922 A | 10/1999 | Arita et al. |
| 5,995,860 A | 11/1999 | Sun et al. |

(56) References Cited

U.S. PATENT DOCUMENTS

| | | |
|---|---|---|
| 6,001,067 A | 12/1999 | Shults et al. |
| 6,016,443 A | 1/2000 | Ekwall et al. |
| 6,021,350 A | 2/2000 | Mathson |
| 6,024,699 A | 2/2000 | Surwit et al. |
| 6,038,469 A | 3/2000 | Karlsson et al. |
| 6,049,727 A | 4/2000 | Crothall |
| 6,071,391 A | 6/2000 | Gotoh et al. |
| 6,073,031 A | 6/2000 | Helstab et al. |
| 6,083,710 A | 7/2000 | Heller et al. |
| 6,088,608 A | 7/2000 | Schulman et al. |
| 6,091,976 A | 7/2000 | Pfeiffer et al. |
| 6,091,987 A | 7/2000 | Thompson |
| 6,093,172 A | 7/2000 | Funderburk et al. |
| 6,096,268 A | 8/2000 | Inbar |
| 6,103,033 A | 8/2000 | Say et al. |
| 6,108,577 A | 8/2000 | Benser |
| 6,112,116 A | 8/2000 | Fischell |
| 6,115,622 A | 9/2000 | Minoz |
| 6,115,628 A | 9/2000 | Stadler et al. |
| 6,117,290 A | 9/2000 | Say et al. |
| 6,119,028 A | 9/2000 | Schulman et al. |
| 6,120,676 A | 9/2000 | Heller et al. |
| 6,121,009 A | 9/2000 | Heller et al. |
| 6,121,611 A | 9/2000 | Lindsay et al. |
| 6,122,351 A | 9/2000 | Schlueter, Jr. et al. |
| 6,128,520 A | 10/2000 | Minoz |
| 6,128,526 A | 10/2000 | Stadler et al. |
| 6,130,623 A | 10/2000 | MacLellan et al. |
| 6,134,461 A | 10/2000 | Say et al. |
| 6,143,164 A | 11/2000 | Heller et al. |
| 6,144,837 A | 11/2000 | Quy |
| 6,144,871 A | 11/2000 | Saito et al. |
| 6,159,147 A | 12/2000 | Lichter et al. |
| 6,161,095 A | 12/2000 | Brown |
| 6,162,611 A | 12/2000 | Heller et al. |
| 6,175,752 B1 | 1/2001 | Say et al. |
| 6,200,265 B1 | 3/2001 | Walsh et al. |
| 6,212,416 B1 | 4/2001 | Ward et al. |
| 6,219,574 B1 | 4/2001 | Cormier et al. |
| 6,223,283 B1 | 4/2001 | Chaiken et al. |
| 6,233,471 B1 | 5/2001 | Berner et al. |
| 6,233,486 B1 | 5/2001 | Ekwall et al. |
| 6,248,067 B1 | 6/2001 | Causey, III et al. |
| 6,249,705 B1 | 6/2001 | Snell |
| 6,254,586 B1 | 7/2001 | Mann et al. |
| 6,256,538 B1 | 7/2001 | Ekwall |
| 6,264,606 B1 | 7/2001 | Ekwall et al. |
| 6,270,455 B1 | 8/2001 | Brown |
| 6,272,379 B1 | 8/2001 | Fischell et al. |
| 6,275,717 B1 | 8/2001 | Gross et al. |
| 6,283,761 B1 | 9/2001 | Joao |
| 6,284,478 B1 | 9/2001 | Heller et al. |
| 6,291,200 B1 | 9/2001 | LeJeune et al. |
| 6,293,925 B1 | 9/2001 | Safabash et al. |
| 6,294,997 B1 | 9/2001 | Paratore et al. |
| 6,295,506 B1 | 9/2001 | Heinonen et al. |
| 6,299,757 B1 | 10/2001 | Feldman et al. |
| 6,306,104 B1 | 10/2001 | Cunningham et al. |
| 6,309,884 B1 | 10/2001 | Cooper et al. |
| 6,329,161 B1 | 12/2001 | Heller et al. |
| 6,338,790 B1 | 1/2002 | Feldman et al. |
| 6,348,640 B1 | 2/2002 | Navot et al. |
| 6,359,444 B1 | 3/2002 | Grimes |
| 6,360,888 B1 | 3/2002 | McIvor et al. |
| 6,361,503 B1 | 3/2002 | Starobin et al. |
| 6,366,794 B1 | 4/2002 | Moussy et al. |
| 6,377,828 B1 | 4/2002 | Chaiken et al. |
| 6,377,852 B1 | 4/2002 | Bornzin et al. |
| 6,377,894 B1 | 4/2002 | Deweese et al. |
| 6,379,301 B1 | 4/2002 | Worthington et al. |
| 6,381,493 B1 | 4/2002 | Stadler et al. |
| 6,387,048 B1 | 5/2002 | Schulman et al. |
| 6,400,974 B1 | 6/2002 | Lesho |
| 6,405,066 B1 | 6/2002 | Essenpreis et al. |
| 6,413,393 B1 | 7/2002 | Van Antwerp et al. |
| 6,416,471 B1 | 7/2002 | Kumar et al. |
| 6,418,346 B1 | 7/2002 | Nelson et al. |
| 6,424,847 B1 | 7/2002 | Mastrototaro et al. |
| 6,427,088 B1 | 7/2002 | Bowman, IV et al. |
| 6,440,068 B1 | 8/2002 | Brown et al. |
| 6,461,496 B1 | 10/2002 | Feldman et al. |
| 6,471,689 B1 | 10/2002 | Joseph et al. |
| 6,478,736 B1 | 11/2002 | Mault |
| 6,484,046 B1 | 11/2002 | Say et al. |
| 6,496,729 B2 | 12/2002 | Thompson |
| 6,497,655 B1 | 12/2002 | Linberg et al. |
| 6,501,983 B1 | 12/2002 | Natarajan et al. |
| 6,503,381 B1 | 1/2003 | Gotoh et al. |
| 6,514,460 B1 | 2/2003 | Fendrock |
| 6,514,718 B2 | 2/2003 | Heller et al. |
| 6,520,326 B2 | 2/2003 | McIvor et al. |
| 6,540,891 B1 | 4/2003 | Stewart et al. |
| 6,544,212 B2 | 4/2003 | Galley et al. |
| 6,549,796 B2 | 4/2003 | Sohrab |
| 6,551,494 B1 | 4/2003 | Heller et al. |
| 6,558,320 B1 | 5/2003 | Causey, III et al. |
| 6,558,321 B1 | 5/2003 | Burd et al. |
| 6,558,351 B1 | 5/2003 | Steil et al. |
| 6,560,471 B1 | 5/2003 | Heller et al. |
| 6,561,975 B1 | 5/2003 | Pool et al. |
| 6,561,978 B1 | 5/2003 | Conn et al. |
| 6,562,001 B2 | 5/2003 | Lebel et al. |
| 6,564,105 B2 | 5/2003 | Starkweather et al. |
| 6,565,509 B1 | 5/2003 | Say et al. |
| 6,571,128 B2 | 5/2003 | Lebel et al. |
| 6,572,542 B1 | 6/2003 | Houben et al. |
| 6,574,490 B2 | 6/2003 | Abbink et al. |
| 6,574,510 B2 | 6/2003 | Von Arx et al. |
| 6,576,101 B1 | 6/2003 | Heller et al. |
| 6,577,899 B2 | 6/2003 | Lebel et al. |
| 6,579,231 B1 | 6/2003 | Phipps |
| 6,579,690 B1 | 6/2003 | Bonnecaze et al. |
| 6,585,644 B2 | 7/2003 | Lebel et al. |
| 6,591,125 B1 | 7/2003 | Buse et al. |
| 6,592,745 B1 | 7/2003 | Feldman et al. |
| 6,595,919 B2 | 7/2003 | Berner et al. |
| 6,600,997 B2 | 7/2003 | Deweese et al. |
| 6,605,200 B1 | 8/2003 | Mao et al. |
| 6,605,201 B1 | 8/2003 | Mao et al. |
| 6,607,509 B2 | 8/2003 | Bobroff et al. |
| 6,610,012 B2 | 8/2003 | Mault |
| 6,616,819 B1 | 9/2003 | Liamos et al. |
| 6,618,934 B1 | 9/2003 | Feldman et al. |
| 6,622,045 B2 | 9/2003 | Snell et al. |
| 6,633,772 B2 | 10/2003 | Ford et al. |
| 6,635,014 B2 | 10/2003 | Starkweather et al. |
| 6,635,167 B1 | 10/2003 | Batman et al. |
| 6,641,533 B2 | 11/2003 | Causey, III et al. |
| 6,648,821 B2 | 11/2003 | Lebel et al. |
| 6,650,471 B2 | 11/2003 | Doi |
| 6,654,625 B1 | 11/2003 | Say et al. |
| 6,656,114 B1 | 12/2003 | Poulson et al. |
| 6,658,396 B1 | 12/2003 | Tang et al. |
| 6,659,948 B2 | 12/2003 | Lebel et al. |
| 6,668,196 B1 | 12/2003 | Villegas et al. |
| 6,675,030 B2 | 1/2004 | Ciuczak et al. |
| 6,676,816 B2 | 1/2004 | Mao et al. |
| 6,687,546 B2 | 2/2004 | Lebel et al. |
| 6,689,056 B1 | 2/2004 | Kilcoyne et al. |
| 6,694,191 B2 | 2/2004 | Starkweather et al. |
| 6,695,860 B1 | 2/2004 | Ward et al. |
| 6,698,269 B2 | 3/2004 | Baber et al. |
| 6,702,857 B2 | 3/2004 | Brauker et al. |
| 6,730,200 B1 | 5/2004 | Stewart et al. |
| 6,731,976 B2 | 5/2004 | Penn et al. |
| 6,731,985 B2 | 5/2004 | Poore et al. |
| 6,733,446 B2 | 5/2004 | Lebel et al. |
| 6,735,183 B2 | 5/2004 | O'Toole et al. |
| 6,736,957 B1 | 5/2004 | Forrow et al. |
| 6,740,075 B2 | 5/2004 | Lebel et al. |
| 6,741,877 B1 | 5/2004 | Shults et al. |
| 6,746,582 B2 | 6/2004 | Heller et al. |
| 6,749,740 B2 | 6/2004 | Liamos et al. |
| 6,758,810 B2 | 7/2004 | Lebel et al. |

(56) References Cited

U.S. PATENT DOCUMENTS

| | | |
|---|---|---|
| 6,764,581 B1 | 7/2004 | Forrow et al. |
| 6,770,030 B1 | 8/2004 | Schaupp et al. |
| 6,773,671 B1 | 8/2004 | Lewis et al. |
| 6,790,178 B1 | 9/2004 | Mault et al. |
| 6,804,558 B2 | 10/2004 | Haller et al. |
| 6,809,653 B1 | 10/2004 | Mann et al. |
| 6,810,290 B2 | 10/2004 | Lebel et al. |
| 6,811,533 B2 | 11/2004 | Lebel et al. |
| 6,811,534 B2 | 11/2004 | Bowman, IV et al. |
| 6,813,519 B2 | 11/2004 | Lebel et al. |
| 6,850,790 B2 | 2/2005 | Berner et al. |
| 6,862,465 B2 | 3/2005 | Shults et al. |
| 6,865,407 B2 | 3/2005 | Kimball et al. |
| 6,873,268 B2 | 3/2005 | Lebel et al. |
| 6,878,112 B2 | 4/2005 | Linberg et al. |
| 6,881,551 B2 | 4/2005 | Heller et al. |
| 6,882,940 B2 | 4/2005 | Potts et al. |
| 6,892,085 B2 | 5/2005 | McIvor et al. |
| 6,893,545 B2 | 5/2005 | Gotoh et al. |
| 6,895,263 B2 | 5/2005 | Shin et al. |
| 6,895,265 B2 | 5/2005 | Silver |
| 6,912,413 B2 | 6/2005 | Rantala et al. |
| 6,923,763 B1 | 8/2005 | Kovatchev et al. |
| 6,923,764 B2 | 8/2005 | Aceti et al. |
| 6,931,327 B2 | 8/2005 | Goode, Jr. et al. |
| 6,932,892 B2 | 8/2005 | Chen et al. |
| 6,932,894 B2 | 8/2005 | Mao et al. |
| 6,936,006 B2 | 8/2005 | Sabra |
| 6,940,403 B2 | 9/2005 | Kail, IV |
| 6,941,163 B2 | 9/2005 | Ford et al. |
| 6,942,518 B2 | 9/2005 | Liamos et al. |
| 6,950,708 B2 | 9/2005 | Bowman IV et al. |
| 6,958,705 B2 | 10/2005 | Lebel et al. |
| 6,968,294 B2 | 11/2005 | Gutta et al. |
| 6,971,274 B2 | 12/2005 | Olin |
| 6,974,437 B2 | 12/2005 | Lebel et al. |
| 6,990,366 B2 | 1/2006 | Say et al. |
| 6,997,907 B2 | 2/2006 | Safabash et al. |
| 6,998,247 B2 | 2/2006 | Monfre et al. |
| 7,003,336 B2 | 2/2006 | Holker et al. |
| 7,003,340 B2 | 2/2006 | Say et al. |
| 7,003,341 B2 | 2/2006 | Say et al. |
| 7,009,511 B2 | 3/2006 | Mazar et al. |
| 7,010,345 B2 | 3/2006 | Hill et al. |
| 7,011,630 B2 | 3/2006 | Desai et al. |
| 7,016,713 B2 | 3/2006 | Gardner et al. |
| 7,016,720 B2 | 3/2006 | Kroll |
| 7,020,508 B2 | 3/2006 | Stivoric et al. |
| 7,022,072 B2 | 4/2006 | Fox et al. |
| 7,022,219 B2 | 4/2006 | Mansouri et al. |
| 7,024,236 B2 | 4/2006 | Ford et al. |
| 7,024,245 B2 | 4/2006 | Lebel et al. |
| 7,025,425 B2 | 4/2006 | Kovatchev et al. |
| 7,029,443 B2 | 4/2006 | Kroll |
| 7,029,444 B2 | 4/2006 | Shin et al. |
| 7,041,068 B2 | 5/2006 | Freeman et al. |
| 7,041,468 B2 | 5/2006 | Drucker et al. |
| 7,043,287 B1 | 5/2006 | Khalil et al. |
| 7,043,305 B2 | 5/2006 | KenKnight et al. |
| 7,052,483 B2 | 5/2006 | Wojcik |
| 7,056,302 B2 | 6/2006 | Douglas |
| 7,058,453 B2 | 6/2006 | Nelson et al. |
| 7,060,031 B2 | 6/2006 | Webb et al. |
| 7,074,307 B2 | 7/2006 | Simpson et al. |
| 7,076,300 B1 | 7/2006 | Kroll et al. |
| 7,081,195 B2 | 7/2006 | Simpson et al. |
| 7,082,334 B2 | 7/2006 | Boute et al. |
| 7,092,891 B2 | 8/2006 | Maus et al. |
| 7,096,064 B2 | 8/2006 | Deno et al. |
| 7,098,803 B2 | 8/2006 | Mann et al. |
| 7,103,412 B1 | 9/2006 | Kroll |
| 7,108,778 B2 | 9/2006 | Simpson et al. |
| 7,110,803 B2 | 9/2006 | Shults et al. |
| 7,113,821 B1 | 9/2006 | Sun et al. |
| 7,118,667 B2 | 10/2006 | Lee |
| 7,123,950 B2 | 10/2006 | Mannheimer |
| 7,125,382 B2 | 10/2006 | Zhou et al. |
| 7,134,999 B2 | 11/2006 | Brauker et al. |
| 7,136,689 B2 | 11/2006 | Shults et al. |
| 7,142,911 B2 | 11/2006 | Boileau et al. |
| 7,153,265 B2 | 12/2006 | Vachon |
| 7,167,818 B2 | 1/2007 | Brown |
| 7,171,274 B2 | 1/2007 | Starkweather et al. |
| 7,190,988 B2 | 3/2007 | Say et al. |
| 7,192,450 B2 | 3/2007 | Brauker et al. |
| 7,198,606 B2 | 4/2007 | Boecker et al. |
| 7,203,549 B2 | 4/2007 | Schommer et al. |
| 7,225,535 B2 | 6/2007 | Feldman et al. |
| 7,226,978 B2 | 6/2007 | Tapsak et al. |
| 7,228,182 B2 | 6/2007 | Healy et al. |
| 7,237,712 B2 | 7/2007 | DeRocco et al. |
| 7,258,673 B2 | 8/2007 | Racchini et al. |
| 7,267,665 B2 | 9/2007 | Steil et al. |
| 7,272,436 B2 | 9/2007 | Gill et al. |
| 7,276,029 B2 | 10/2007 | Goode, Jr. et al. |
| 7,278,983 B2 | 10/2007 | Ireland et al. |
| 7,295,867 B2 | 11/2007 | Berner et al. |
| 7,297,114 B2 | 11/2007 | Gill et al. |
| 7,299,082 B2 | 11/2007 | Feldman et al. |
| 7,310,544 B2 | 12/2007 | Brister et al. |
| 7,317,938 B2 | 1/2008 | Lorenz et al. |
| 7,318,816 B2 | 1/2008 | Bobroff et al. |
| 7,324,012 B2 | 1/2008 | Mann et al. |
| 7,324,850 B2 | 1/2008 | Persen et al. |
| 7,335,294 B2 | 2/2008 | Heller et al. |
| 7,347,819 B2 | 3/2008 | Lebel et al. |
| 7,354,420 B2 | 4/2008 | Steil et al. |
| 7,364,592 B2 | 4/2008 | Carr-Brendel et al. |
| 7,366,556 B2 | 4/2008 | Brister et al. |
| 7,379,765 B2 | 5/2008 | Petisce et al. |
| 7,384,397 B2 | 6/2008 | Zhang et al. |
| 7,387,010 B2 | 6/2008 | Sunshine et al. |
| 7,399,277 B2 | 7/2008 | Saidara et al. |
| 7,402,153 B2 | 7/2008 | Steil et al. |
| 7,404,796 B2 | 7/2008 | Ginsberg |
| 7,419,573 B2 | 9/2008 | Gundel |
| 7,424,318 B2 | 9/2008 | Brister et al. |
| 7,460,898 B2 | 12/2008 | Brister et al. |
| 7,467,003 B2 | 12/2008 | Brister et al. |
| 7,468,125 B2 | 12/2008 | Kraft et al. |
| 7,471,972 B2 | 12/2008 | Rhodes et al. |
| 7,474,992 B2 | 1/2009 | Ariyur |
| 7,492,254 B2 | 2/2009 | Bandy et al. |
| 7,494,465 B2 | 2/2009 | Brister et al. |
| 7,497,827 B2 | 3/2009 | Brister et al. |
| 7,499,002 B2 | 3/2009 | Blasko et al. |
| 7,502,644 B2 | 3/2009 | Gill et al. |
| 7,519,408 B2 | 4/2009 | Rasdal et al. |
| 7,524,287 B2 | 4/2009 | Bharmi |
| 7,547,281 B2 | 6/2009 | Hayes et al. |
| 7,565,197 B2 | 7/2009 | Haubrich et al. |
| 7,569,030 B2 | 8/2009 | Lebel et al. |
| 7,574,266 B2 | 8/2009 | Dudding et al. |
| 7,583,990 B2 | 9/2009 | Goode, Jr. et al. |
| 7,591,801 B2 | 9/2009 | Brauker et al. |
| 7,599,726 B2 | 10/2009 | Goode, Jr. et al. |
| 7,602,310 B2 | 10/2009 | Mann et al. |
| 7,604,178 B2 | 10/2009 | Stewart |
| 7,613,491 B2 | 11/2009 | Boock et al. |
| 7,615,007 B2 | 11/2009 | Shults et al. |
| 7,618,369 B2 | 11/2009 | Hayter et al. |
| 7,630,748 B2 | 12/2009 | Budiman |
| 7,632,228 B2 | 12/2009 | Brauker et al. |
| 7,635,594 B2 | 12/2009 | Holmes et al. |
| 7,637,868 B2 | 12/2009 | Saint et al. |
| 7,640,048 B2 | 12/2009 | Dobbles et al. |
| 7,643,798 B2 | 1/2010 | Ljung |
| 7,659,823 B1 | 2/2010 | Killian et al. |
| 7,668,596 B2 | 2/2010 | Von Arx et al. |
| 7,699,775 B2 | 4/2010 | Desai et al. |
| 7,699,964 B2 | 4/2010 | Feldman et al. |
| 7,736,310 B2 | 6/2010 | Taub et al. |
| 7,741,734 B2 | 6/2010 | Joannopoulos et al. |
| 7,766,829 B2 | 8/2010 | Sloan et al. |

(56) References Cited

U.S. PATENT DOCUMENTS

| | | |
|---|---|---|
| 7,771,352 B2 | 8/2010 | Shults et al. |
| 7,774,145 B2 | 8/2010 | Bruaker et al. |
| 7,778,680 B2 | 8/2010 | Goode, Jr. et al. |
| 7,779,332 B2 | 8/2010 | Karr et al. |
| 7,782,192 B2 | 8/2010 | Jeckelmann et al. |
| 7,783,333 B2 | 8/2010 | Brister et al. |
| 7,791,467 B2 | 9/2010 | Mazar et al. |
| 7,792,562 B2 | 9/2010 | Shults et al. |
| 7,826,981 B2 | 11/2010 | Goode, Jr. et al. |
| 7,831,310 B2 | 11/2010 | Lebel et al. |
| 7,860,574 B2 | 12/2010 | Von Arx et al. |
| 7,866,026 B1 | 1/2011 | Wang et al. |
| 7,882,611 B2 | 2/2011 | Shah et al. |
| 7,889,069 B2 | 2/2011 | Fifolt et al. |
| 7,899,511 B2 | 3/2011 | Shults et al. |
| 7,905,833 B2 | 3/2011 | Brister et al. |
| 7,912,674 B2 | 3/2011 | Killoren Clark et al. |
| 7,914,450 B2 | 3/2011 | Goode, Jr. et al. |
| 7,916,013 B2 | 3/2011 | Stevenson |
| 7,938,797 B2 | 5/2011 | Estes |
| 7,955,258 B2 | 6/2011 | Goscha et al. |
| 7,970,448 B2 | 6/2011 | Shults et al. |
| 7,974,672 B2 | 7/2011 | Shults et al. |
| 7,999,674 B2 | 8/2011 | Kamen |
| 8,072,310 B1 | 12/2011 | Everhart |
| 8,090,445 B2 | 1/2012 | Ginggen |
| 8,093,991 B2 | 1/2012 | Stevenson et al. |
| 8,094,009 B2 | 1/2012 | Allen et al. |
| 8,098,159 B2 | 1/2012 | Batra et al. |
| 8,098,160 B2 | 1/2012 | Howarth et al. |
| 8,098,161 B2 | 1/2012 | Lavedas |
| 8,098,201 B2 | 1/2012 | Choi et al. |
| 8,098,208 B2 | 1/2012 | Ficker et al. |
| 8,102,021 B2 | 1/2012 | Degani |
| 8,102,154 B2 | 1/2012 | Bishop et al. |
| 8,102,263 B2 | 1/2012 | Yeo et al. |
| 8,102,789 B2 | 1/2012 | Rosar et al. |
| 8,103,241 B2 | 1/2012 | Young et al. |
| 8,103,325 B2 | 1/2012 | Swedlow et al. |
| 8,111,042 B2 | 2/2012 | Bennett |
| 8,115,488 B2 | 2/2012 | McDowell |
| 8,116,681 B2 | 2/2012 | Baarman |
| 8,116,683 B2 | 2/2012 | Baarman |
| 8,116,837 B2 | 2/2012 | Huang |
| 8,116,936 B2 | 2/2012 | Hershey et al. |
| 8,117,481 B2 | 2/2012 | Anselmi et al. |
| 8,120,493 B2 | 2/2012 | Burr |
| 8,124,452 B2 | 2/2012 | Sheats |
| 8,130,093 B2 | 3/2012 | Mazar et al. |
| 8,131,351 B2 | 3/2012 | Kalgren et al. |
| 8,131,365 B2 | 3/2012 | Zhang et al. |
| 8,131,565 B2 | 3/2012 | Dicks et al. |
| 8,132,037 B2 | 3/2012 | Fehr et al. |
| 8,135,352 B2 | 3/2012 | Langsweirdt et al. |
| 8,136,735 B2 | 3/2012 | Arai et al. |
| 8,138,925 B2 | 3/2012 | Downie et al. |
| 8,140,160 B2 | 3/2012 | Pless et al. |
| 8,140,168 B2 | 3/2012 | Olson et al. |
| 8,140,299 B2 | 3/2012 | Siess |
| 8,150,321 B2 | 4/2012 | Winter et al. |
| 8,150,516 B2 | 4/2012 | Levine et al. |
| 8,160,900 B2 | 4/2012 | Taub et al. |
| 8,179,266 B2 | 5/2012 | Hermle |
| 8,216,138 B1 | 7/2012 | McGarraugh et al. |
| 8,224,415 B2 | 7/2012 | Budiman et al. |
| 8,231,531 B2 | 7/2012 | Brister et al. |
| 8,255,026 B1 | 8/2012 | Al-Ali |
| 8,282,549 B2 | 10/2012 | Brauker et al. |
| 8,457,703 B2 | 6/2013 | Al-Ali |
| 8,532,935 B2 | 9/2013 | Budiman |
| 8,764,651 B2 | 7/2014 | Tran |
| 8,771,183 B2 | 7/2014 | Sloan |
| 9,241,631 B2 | 1/2016 | Valdes et al. |
| 9,577,934 B2 | 2/2017 | Gross |
| 9,996,668 B2 | 6/2018 | Reihman et al. |
| 10,085,640 B2 | 10/2018 | Mensinger et al. |
| 10,827,954 B2 | 11/2020 | Hoss et al. |
| 10,973,443 B2 | 4/2021 | Funderburk et al. |
| 10,980,461 B2 | 4/2021 | Simpson et al. |
| 11,000,213 B2 | 5/2021 | Kamath et al. |
| 11,064,917 B2 | 7/2021 | Simpson et al. |
| 11,141,084 B2 | 10/2021 | Funderburk et al. |
| 11,298,056 B2 | 4/2022 | Harper |
| 11,563,812 B2 | 1/2023 | Sloan et al. |
| 2001/0041831 A1 | 11/2001 | Starkweather et al. |
| 2002/0019022 A1 | 2/2002 | Dunn et al. |
| 2002/0042090 A1 | 4/2002 | Heller et al. |
| 2002/0065454 A1 | 5/2002 | Lebel et al. |
| 2002/0068860 A1 | 6/2002 | Clark |
| 2002/0072784 A1 | 6/2002 | Sheppard et al. |
| 2002/0103499 A1 | 8/2002 | Perez et al. |
| 2002/0106709 A1 | 8/2002 | Potts et al. |
| 2002/0120186 A1 | 8/2002 | Keimel |
| 2002/0128594 A1 | 9/2002 | Das et al. |
| 2002/0143266 A1 | 10/2002 | Bock |
| 2002/0143372 A1 | 10/2002 | Snell et al. |
| 2002/0161288 A1 | 10/2002 | Shin et al. |
| 2002/0169635 A1 | 11/2002 | Shillingburg |
| 2002/0193679 A1 | 12/2002 | Malave et al. |
| 2003/0004403 A1 | 1/2003 | Drinan et al. |
| 2003/0023317 A1 | 1/2003 | Brauker et al. |
| 2003/0023461 A1 | 1/2003 | Quintanilla et al. |
| 2003/0028184 A1 | 2/2003 | Lebel et al. |
| 2003/0032867 A1 | 2/2003 | Crothall et al. |
| 2003/0032874 A1 | 2/2003 | Rhodes et al. |
| 2003/0042137 A1 | 3/2003 | Mao et al. |
| 2003/0050546 A1 | 3/2003 | Desai et al. |
| 2003/0065308 A1 | 4/2003 | Lebel et al. |
| 2003/0065536 A1 | 4/2003 | Hansen et al. |
| 2003/0100821 A1 | 5/2003 | Heller et al. |
| 2003/0125612 A1 | 7/2003 | Fox et al. |
| 2003/0130616 A1 | 7/2003 | Steil et al. |
| 2003/0134347 A1 | 7/2003 | Heller et al. |
| 2003/0144581 A1 | 7/2003 | Conn et al. |
| 2003/0153820 A1 | 8/2003 | Aceti et al. |
| 2003/0168338 A1 | 9/2003 | Gao et al. |
| 2003/0176933 A1 | 9/2003 | Lebel et al. |
| 2003/0187338 A1 | 10/2003 | Say et al. |
| 2003/0191377 A1 | 10/2003 | Robinson et al. |
| 2003/0199744 A1 | 10/2003 | Buse et al. |
| 2003/0199790 A1 | 10/2003 | Boecker et al. |
| 2003/0208113 A1 | 11/2003 | Mault et al. |
| 2003/0212317 A1 | 11/2003 | Kovatchev et al. |
| 2003/0212379 A1 | 11/2003 | Bylund et al. |
| 2003/0216630 A1 | 11/2003 | Jersey-Willuhn et al. |
| 2003/0217966 A1 | 11/2003 | Tapsak et al. |
| 2004/0010186 A1 | 1/2004 | Kimball et al. |
| 2004/0010207 A1 | 1/2004 | Flaherty et al. |
| 2004/0011671 A1 | 1/2004 | Shults et al. |
| 2004/0024553 A1 | 2/2004 | Monfre et al. |
| 2004/0039298 A1 | 2/2004 | Abreu |
| 2004/0040840 A1 | 3/2004 | Mao et al. |
| 2004/0045879 A1 | 3/2004 | Shults et al. |
| 2004/0054263 A1 | 3/2004 | Moerman et al. |
| 2004/0064068 A1 | 4/2004 | DeNuzzio et al. |
| 2004/0077962 A1 | 4/2004 | Kroll |
| 2004/0078065 A1 | 4/2004 | Kroll |
| 2004/0093167 A1 | 5/2004 | Braig et al. |
| 2004/0099529 A1 | 5/2004 | Mao et al. |
| 2004/0106858 A1 | 6/2004 | Say et al. |
| 2004/0122353 A1 | 6/2004 | Shahmirian et al. |
| 2004/0133164 A1 | 7/2004 | Funderburk et al. |
| 2004/0135684 A1 | 7/2004 | Steinthal et al. |
| 2004/0138588 A1 | 7/2004 | Saikley et al. |
| 2004/0138716 A1 | 7/2004 | Kon et al. |
| 2004/0146909 A1 | 7/2004 | Duong et al. |
| 2004/0152622 A1 | 8/2004 | Keith et al. |
| 2004/0167801 A1 | 8/2004 | Say et al. |
| 2004/0171921 A1 | 9/2004 | Say et al. |
| 2004/0172307 A1 | 9/2004 | Gruber |
| 2004/0176672 A1 | 9/2004 | Silver et al. |
| 2004/0186362 A1 | 9/2004 | Brauker et al. |
| 2004/0186365 A1 | 9/2004 | Jin et al. |
| 2004/0193025 A1 | 9/2004 | Steil et al. |

(56) References Cited

U.S. PATENT DOCUMENTS

| | | |
|---|---|---|
| 2004/0193090 A1 | 9/2004 | Lebel et al. |
| 2004/0197846 A1 | 10/2004 | Hockersmith et al. |
| 2004/0199056 A1 | 10/2004 | Husemann et al. |
| 2004/0199059 A1 | 10/2004 | Brauker et al. |
| 2004/0204687 A1 | 10/2004 | Mogensen et al. |
| 2004/0208780 A1 | 10/2004 | Faries, Jr. et al. |
| 2004/0225338 A1 | 11/2004 | Lebel et al. |
| 2004/0236200 A1 | 11/2004 | Say et al. |
| 2004/0249253 A1 | 12/2004 | Racchini et al. |
| 2004/0249420 A1 | 12/2004 | Olson et al. |
| 2004/0254433 A1 | 12/2004 | Bandis et al. |
| 2004/0254434 A1 | 12/2004 | Goodnow et al. |
| 2004/0260478 A1 | 12/2004 | Schwamm |
| 2004/0263354 A1 | 12/2004 | Mann et al. |
| 2004/0267300 A1 | 12/2004 | Mace |
| 2005/0003470 A1 | 1/2005 | Nelson et al. |
| 2005/0004439 A1 | 1/2005 | Shin et al. |
| 2005/0004494 A1 | 1/2005 | Perez et al. |
| 2005/0010087 A1 | 1/2005 | Banet et al. |
| 2005/0010269 A1 | 1/2005 | Lebel et al. |
| 2005/0016276 A1 | 1/2005 | Guan et al. |
| 2005/0017864 A1 | 1/2005 | Tsoukalis |
| 2005/0027177 A1 | 2/2005 | Shin et al. |
| 2005/0027180 A1 | 2/2005 | Goode et al. |
| 2005/0027181 A1 | 2/2005 | Goode et al. |
| 2005/0027462 A1 | 2/2005 | Goode et al. |
| 2005/0027463 A1 | 2/2005 | Goode et al. |
| 2005/0031689 A1 | 2/2005 | Shults et al. |
| 2005/0038332 A1 | 2/2005 | Saidara et al. |
| 2005/0043598 A1 | 2/2005 | Goode, Jr. et al. |
| 2005/0049179 A1 | 3/2005 | Davidson et al. |
| 2005/0070774 A1 | 3/2005 | Addison et al. |
| 2005/0090607 A1 | 4/2005 | Tapsak et al. |
| 2005/0096511 A1 | 5/2005 | Fox et al. |
| 2005/0096512 A1 | 5/2005 | Fox et al. |
| 2005/0112169 A1 | 5/2005 | Brauker et al. |
| 2005/0113653 A1 | 5/2005 | Fox et al. |
| 2005/0114068 A1 | 5/2005 | Chey et al. |
| 2005/0115832 A1 | 6/2005 | Simpson et al. |
| 2005/0121322 A1 | 6/2005 | Say et al. |
| 2005/0131346 A1 | 6/2005 | Douglas |
| 2005/0143635 A1 | 6/2005 | Kamath et al. |
| 2005/0154271 A1 | 7/2005 | Rasdal et al. |
| 2005/0176136 A1 | 8/2005 | Burd et al. |
| 2005/0177398 A1 | 8/2005 | Watanabe et al. |
| 2005/0182306 A1 | 8/2005 | Sloan |
| 2005/0187720 A1 | 8/2005 | Goode, Jr. et al. |
| 2005/0192494 A1 | 9/2005 | Ginsberg |
| 2005/0192557 A1 | 9/2005 | Brauker et al. |
| 2005/0195930 A1 | 9/2005 | Spital et al. |
| 2005/0199494 A1 | 9/2005 | Say et al. |
| 2005/0203360 A1 | 9/2005 | Brauker et al. |
| 2005/0214892 A1 | 9/2005 | Kovatchev et al. |
| 2005/0239154 A1 | 10/2005 | Feldman et al. |
| 2005/0239156 A1 | 10/2005 | Drucker et al. |
| 2005/0241957 A1 | 11/2005 | Mao et al. |
| 2005/0242479 A1 | 11/2005 | Petisce et al. |
| 2005/0245795 A1 | 11/2005 | Goode, Jr. et al. |
| 2005/0245799 A1 | 11/2005 | Brauker et al. |
| 2005/0245839 A1 | 11/2005 | Stivoric et al. |
| 2005/0245904 A1 | 11/2005 | Estes et al. |
| 2005/0277164 A1 | 12/2005 | Drucker et al. |
| 2005/0277912 A1 | 12/2005 | John |
| 2005/0283114 A1 | 12/2005 | Bresina et al. |
| 2005/0283208 A1 | 12/2005 | Von Arx et al. |
| 2005/0287620 A1 | 12/2005 | Heller et al. |
| 2005/0288725 A1 | 12/2005 | Hettrick et al. |
| 2006/0001538 A1 | 1/2006 | Kraft et al. |
| 2006/0004270 A1 | 1/2006 | Bedard et al. |
| 2006/0010098 A1 | 1/2006 | Goodnow et al. |
| 2006/0015020 A1 | 1/2006 | Neale et al. |
| 2006/0015024 A1 | 1/2006 | Brister et al. |
| 2006/0016700 A1 | 1/2006 | Brister et al. |
| 2006/0017923 A1 | 1/2006 | Ruchti et al. |
| 2006/0019327 A1 | 1/2006 | Brister et al. |
| 2006/0020186 A1 | 1/2006 | Brister et al. |
| 2006/0020187 A1 | 1/2006 | Brister et al. |
| 2006/0020188 A1 | 1/2006 | Kamath et al. |
| 2006/0020189 A1 | 1/2006 | Brister et al. |
| 2006/0020190 A1 | 1/2006 | Kamath et al. |
| 2006/0020191 A1 | 1/2006 | Brister et al. |
| 2006/0020192 A1 | 1/2006 | Brister et al. |
| 2006/0025662 A1 | 2/2006 | Buse et al. |
| 2006/0025663 A1 | 2/2006 | Talbot et al. |
| 2006/0029177 A1 | 2/2006 | Cranford, Jr. et al. |
| 2006/0031094 A1 | 2/2006 | Cohen et al. |
| 2006/0036139 A1 | 2/2006 | Brister et al. |
| 2006/0036140 A1 | 2/2006 | Brister et al. |
| 2006/0036141 A1 | 2/2006 | Kamath et al. |
| 2006/0036142 A1 | 2/2006 | Brister et al. |
| 2006/0036143 A1 | 2/2006 | Brister et al. |
| 2006/0036144 A1 | 2/2006 | Brister et al. |
| 2006/0036145 A1 | 2/2006 | Brister et al. |
| 2006/0058588 A1 | 3/2006 | Zdeblick |
| 2006/0091006 A1 | 5/2006 | Wang et al. |
| 2006/0142651 A1 | 6/2006 | Brister et al. |
| 2006/0155180 A1 | 7/2006 | Brister et al. |
| 2006/0166629 A1 | 7/2006 | Reggiardo |
| 2006/0167365 A1 | 7/2006 | Bharmi |
| 2006/0167517 A1 | 7/2006 | Gill et al. |
| 2006/0167518 A1 | 7/2006 | Gill et al. |
| 2006/0167519 A1 | 7/2006 | Gill et al. |
| 2006/0173260 A1 | 8/2006 | Gaoni et al. |
| 2006/0173406 A1 | 8/2006 | Hayes et al. |
| 2006/0173444 A1 | 8/2006 | Choy et al. |
| 2006/0183984 A1 | 8/2006 | Dobbles et al. |
| 2006/0183985 A1 | 8/2006 | Brister et al. |
| 2006/0189851 A1 | 8/2006 | Tvig et al. |
| 2006/0189863 A1 | 8/2006 | Peyser et al. |
| 2006/0193375 A1 | 8/2006 | Lee |
| 2006/0202859 A1 | 9/2006 | Mastrototaro et al. |
| 2006/0222566 A1 | 10/2006 | Brauker et al. |
| 2006/0224109 A1 | 10/2006 | Steil et al. |
| 2006/0226985 A1 | 10/2006 | Goodnow et al. |
| 2006/0229512 A1 | 10/2006 | Petisce et al. |
| 2006/0247508 A1 | 11/2006 | Fennell |
| 2006/0247685 A1 | 11/2006 | Bharmi |
| 2006/0247710 A1 | 11/2006 | Goetz et al. |
| 2006/0247985 A1 | 11/2006 | Liamos et al. |
| 2006/0258929 A1 | 11/2006 | Goode et al. |
| 2006/0264785 A1 | 11/2006 | Dring et al. |
| 2006/0272652 A1 | 12/2006 | Stocker et al. |
| 2006/0281985 A1 | 12/2006 | Ward et al. |
| 2006/0287691 A1 | 12/2006 | Drew |
| 2007/0016381 A1 | 1/2007 | Kamath et al. |
| 2007/0027381 A1 | 2/2007 | Stafford |
| 2007/0032706 A1 | 2/2007 | Kamath et al. |
| 2007/0033074 A1 | 2/2007 | Nitzan et al. |
| 2007/0038044 A1 | 2/2007 | Dobbles et al. |
| 2007/0055799 A1 | 3/2007 | Koehler et al. |
| 2007/0056858 A1 | 3/2007 | Chen et al. |
| 2007/0060803 A1 | 3/2007 | Liljeryd et al. |
| 2007/0060814 A1 | 3/2007 | Stafford |
| 2007/0066873 A1 | 3/2007 | Kamath et al. |
| 2007/0068807 A1 | 3/2007 | Feldman et al. |
| 2007/0071681 A1 | 3/2007 | Gadkar et al. |
| 2007/0073129 A1 | 3/2007 | Shah et al. |
| 2007/0078320 A1 | 4/2007 | Stafford |
| 2007/0078321 A1 | 4/2007 | Mazza et al. |
| 2007/0078322 A1 | 4/2007 | Stafford |
| 2007/0078323 A1 | 4/2007 | Reggiardo et al. |
| 2007/0093786 A1 | 4/2007 | Goldsmith et al. |
| 2007/0095661 A1 | 5/2007 | Wang et al. |
| 2007/0106135 A1 | 5/2007 | Sloan et al. |
| 2007/0108048 A1 | 5/2007 | Wang et al. |
| 2007/0118405 A1 | 5/2007 | Campbell et al. |
| 2007/0124002 A1 | 5/2007 | Estes et al. |
| 2007/0129621 A1 | 6/2007 | Kellogg et al. |
| 2007/0149875 A1 | 6/2007 | Ouyang et al. |
| 2007/0156033 A1 | 7/2007 | Causey, III et al. |
| 2007/0163880 A1 | 7/2007 | Woo et al. |
| 2007/0168224 A1 | 7/2007 | Letzt et al. |
| 2007/0173706 A1 | 7/2007 | Neinast et al. |
| 2007/0173708 A9 | 7/2007 | Dobbles et al. |

(56) References Cited

U.S. PATENT DOCUMENTS

| | | |
|---|---|---|
| 2007/0173709 A1 | 7/2007 | Petisce et al. |
| 2007/0173710 A1 | 7/2007 | Petisce et al. |
| 2007/0173761 A1 | 7/2007 | Kanderian et al. |
| 2007/0179349 A1 | 8/2007 | Hoyme et al. |
| 2007/0179352 A1 | 8/2007 | Randlov et al. |
| 2007/0179434 A1 | 8/2007 | Weinert et al. |
| 2007/0191701 A1 | 8/2007 | Feldman et al. |
| 2007/0199818 A1 | 8/2007 | Petyt et al. |
| 2007/0202562 A1 | 8/2007 | Curry et al. |
| 2007/0203407 A1 | 8/2007 | Hoss et al. |
| 2007/0203966 A1 | 8/2007 | Brauker et al. |
| 2007/0213657 A1 | 9/2007 | Jennewine et al. |
| 2007/0227911 A1 | 10/2007 | Wang et al. |
| 2007/0232877 A1 | 10/2007 | He |
| 2007/0232878 A1 | 10/2007 | Kovatchev et al. |
| 2007/0232880 A1 | 10/2007 | Siddiqui et al. |
| 2007/0233013 A1 | 10/2007 | Schoenberg et al. |
| 2007/0235331 A1 | 10/2007 | Simpson et al. |
| 2007/0244383 A1 | 10/2007 | Talbot et al. |
| 2007/0249922 A1 | 10/2007 | Peyser et al. |
| 2007/0253021 A1 | 11/2007 | Mehta et al. |
| 2007/0255116 A1 | 11/2007 | Mehta et al. |
| 2007/0255321 A1 | 11/2007 | Gerber et al. |
| 2007/0255531 A1 | 11/2007 | Drew |
| 2007/0258395 A1 | 11/2007 | Jollota et al. |
| 2007/0270672 A1 | 11/2007 | Hayter |
| 2007/0282299 A1 | 12/2007 | Hellwig |
| 2007/0285238 A1 | 12/2007 | Batra |
| 2007/0299617 A1 | 12/2007 | Willis |
| 2008/0004515 A1 | 1/2008 | Jennewine et al. |
| 2008/0004601 A1 | 1/2008 | Jennewine et al. |
| 2008/0009692 A1 | 1/2008 | Stafford |
| 2008/0009805 A1 | 1/2008 | Ethelfeld |
| 2008/0017522 A1 | 1/2008 | Heller et al. |
| 2008/0018433 A1 | 1/2008 | Pitt-Pladdy |
| 2008/0021666 A1 | 1/2008 | Goode, Jr. et al. |
| 2008/0029391 A1 | 2/2008 | Mao et al. |
| 2008/0030369 A1 | 2/2008 | Mann et al. |
| 2008/0033254 A1 | 2/2008 | Kamath et al. |
| 2008/0039702 A1 | 2/2008 | Hayter et al. |
| 2008/0045824 A1 | 2/2008 | Tapsak et al. |
| 2008/0058625 A1 | 3/2008 | McGarraugh et al. |
| 2008/0064937 A1 | 3/2008 | McGarraugh et al. |
| 2008/0064943 A1 | 3/2008 | Talbot et al. |
| 2008/0066305 A1 | 3/2008 | Wang et al. |
| 2008/0071156 A1 | 3/2008 | Brister et al. |
| 2008/0071157 A1 | 3/2008 | McGarraugh et al. |
| 2008/0071158 A1 | 3/2008 | McGarraugh et al. |
| 2008/0071328 A1 | 3/2008 | Haubrich et al. |
| 2008/0081977 A1 | 4/2008 | Hayter et al. |
| 2008/0083617 A1 | 4/2008 | Simpson et al. |
| 2008/0086042 A1 | 4/2008 | Brister et al. |
| 2008/0086044 A1 | 4/2008 | Brister et al. |
| 2008/0086273 A1 | 4/2008 | Shults et al. |
| 2008/0092638 A1 | 4/2008 | Brenneman et al. |
| 2008/0097289 A1 | 4/2008 | Steil et al. |
| 2008/0102441 A1 | 5/2008 | Chen et al. |
| 2008/0108942 A1 | 5/2008 | Brister et al. |
| 2008/0119703 A1 | 5/2008 | Brister et al. |
| 2008/0119705 A1 | 5/2008 | Patel et al. |
| 2008/0119708 A1 | 5/2008 | Budiman |
| 2008/0139910 A1 | 6/2008 | Mastrototaro et al. |
| 2008/0148873 A1 | 6/2008 | Wang |
| 2008/0154513 A1 | 6/2008 | Kovatchev et al. |
| 2008/0161666 A1 | 7/2008 | Feldman et al. |
| 2008/0167543 A1 | 7/2008 | Say et al. |
| 2008/0167572 A1 | 7/2008 | Stivoric et al. |
| 2008/0172205 A1 | 7/2008 | Breton et al. |
| 2008/0177149 A1 | 7/2008 | Weinert et al. |
| 2008/0177165 A1 | 7/2008 | Blomquist et al. |
| 2008/0183060 A1 | 7/2008 | Steil et al. |
| 2008/0183061 A1 | 7/2008 | Goode et al. |
| 2008/0183399 A1 | 7/2008 | Goode et al. |
| 2008/0188731 A1 | 8/2008 | Brister et al. |
| 2008/0188796 A1 | 8/2008 | Steil et al. |
| 2008/0189051 A1 | 8/2008 | Goode et al. |
| 2008/0194934 A1 | 8/2008 | Ray et al. |
| 2008/0194935 A1 | 8/2008 | Brister et al. |
| 2008/0194936 A1 | 8/2008 | Goode et al. |
| 2008/0194937 A1 | 8/2008 | Goode et al. |
| 2008/0194938 A1 | 8/2008 | Brister et al. |
| 2008/0195232 A1 | 8/2008 | Carr-Brendel et al. |
| 2008/0195967 A1 | 8/2008 | Goode et al. |
| 2008/0197024 A1 | 8/2008 | Simpson et al. |
| 2008/0200788 A1 | 8/2008 | Brister et al. |
| 2008/0200789 A1 | 8/2008 | Brister et al. |
| 2008/0200791 A1 | 8/2008 | Simpson et al. |
| 2008/0201325 A1 | 8/2008 | Doniger et al. |
| 2008/0208025 A1 | 8/2008 | Shults et al. |
| 2008/0208113 A1 | 8/2008 | Damiano et al. |
| 2008/0214900 A1 | 9/2008 | Fennell et al. |
| 2008/0214910 A1 | 9/2008 | Buck |
| 2008/0214915 A1 | 9/2008 | Brister et al. |
| 2008/0214918 A1 | 9/2008 | Brister et al. |
| 2008/0228045 A1 | 9/2008 | Gao et al. |
| 2008/0228051 A1 | 9/2008 | Shults et al. |
| 2008/0228054 A1 | 9/2008 | Shults et al. |
| 2008/0234943 A1 | 9/2008 | Ray et al. |
| 2008/0235469 A1 | 9/2008 | Drew |
| 2008/0242961 A1 | 10/2008 | Brister et al. |
| 2008/0242963 A1 | 10/2008 | Essenpreis et al. |
| 2008/0255434 A1 | 10/2008 | Hayter et al. |
| 2008/0255437 A1 | 10/2008 | Hayter |
| 2008/0255438 A1 | 10/2008 | Saidara et al. |
| 2008/0255808 A1 | 10/2008 | Hayter |
| 2008/0256048 A1 | 10/2008 | Hayter |
| 2008/0262469 A1 | 10/2008 | Brister et al. |
| 2008/0267823 A1 | 10/2008 | Wang et al. |
| 2008/0275313 A1 | 11/2008 | Brister et al. |
| 2008/0278333 A1 | 11/2008 | Fennell et al. |
| 2008/0287761 A1 | 11/2008 | Hayter |
| 2008/0287762 A1 | 11/2008 | Hayter |
| 2008/0287763 A1 | 11/2008 | Hayter |
| 2008/0287764 A1 | 11/2008 | Rasdal et al. |
| 2008/0287765 A1 | 11/2008 | Rasdal et al. |
| 2008/0287766 A1 | 11/2008 | Rasdal et al. |
| 2008/0288180 A1 | 11/2008 | Hayter |
| 2008/0288204 A1 | 11/2008 | Hayter et al. |
| 2008/0296155 A1 | 12/2008 | Shults et al. |
| 2008/0300572 A1 | 12/2008 | Rankers et al. |
| 2008/0306368 A1 | 12/2008 | Goode et al. |
| 2008/0306434 A1 | 12/2008 | Dobbles et al. |
| 2008/0306435 A1 | 12/2008 | Kamath et al. |
| 2008/0306444 A1 | 12/2008 | Brister et al. |
| 2008/0312518 A1 | 12/2008 | Jina et al. |
| 2008/0312841 A1 | 12/2008 | Hayter |
| 2008/0312842 A1 | 12/2008 | Hayter |
| 2008/0312844 A1 | 12/2008 | Hayter et al. |
| 2008/0312845 A1 | 12/2008 | Hayter et al. |
| 2008/0314395 A1 | 12/2008 | Kovatchev et al. |
| 2008/0319279 A1 | 12/2008 | Ramsay et al. |
| 2009/0005665 A1 | 1/2009 | Hayter et al. |
| 2009/0005666 A1 | 1/2009 | Shin et al. |
| 2009/0006034 A1 | 1/2009 | Hayter et al. |
| 2009/0006061 A1 | 1/2009 | Thukral et al. |
| 2009/0006133 A1 | 1/2009 | Weinert et al. |
| 2009/0012376 A1 | 1/2009 | Agus |
| 2009/0012379 A1 | 1/2009 | Goode et al. |
| 2009/0018424 A1 | 1/2009 | Kamath et al. |
| 2009/0018425 A1 | 1/2009 | Ouyang et al. |
| 2009/0030293 A1 | 1/2009 | Cooper et al. |
| 2009/0030294 A1 | 1/2009 | Petisce et al. |
| 2009/0033482 A1 | 2/2009 | Hayter et al. |
| 2009/0033485 A1 | 2/2009 | Hayter et al. |
| 2009/0036747 A1 | 2/2009 | Hayter et al. |
| 2009/0036758 A1 | 2/2009 | Brauker et al. |
| 2009/0036760 A1 | 2/2009 | Hayter |
| 2009/0036763 A1 | 2/2009 | Brauker et al. |
| 2009/0043181 A1 | 2/2009 | Brauker et al. |
| 2009/0043182 A1 | 2/2009 | Brauker et al. |
| 2009/0043525 A1 | 2/2009 | Brauker et al. |
| 2009/0043541 A1 | 2/2009 | Brauker et al. |
| 2009/0043542 A1 | 2/2009 | Brauker et al. |
| 2009/0045055 A1 | 2/2009 | Rhodes et al. |

(56) References Cited

U.S. PATENT DOCUMENTS

| | | |
|---|---|---|
| 2009/0048503 A1 | 2/2009 | Dalal et al. |
| 2009/0054737 A1 | 2/2009 | Magar et al. |
| 2009/0054745 A1 | 2/2009 | Jennewine et al. |
| 2009/0054748 A1 | 2/2009 | Feldman et al. |
| 2009/0054753 A1 | 2/2009 | Robinson et al. |
| 2009/0055149 A1 | 2/2009 | Hayter et al. |
| 2009/0062633 A1 | 3/2009 | Brauker et al. |
| 2009/0062635 A1 | 3/2009 | Brauker et al. |
| 2009/0062767 A1 | 3/2009 | VanAntwerp et al. |
| 2009/0063402 A1 | 3/2009 | Hayter |
| 2009/0076356 A1 | 3/2009 | Simpson et al. |
| 2009/0076360 A1 | 3/2009 | Brister et al. |
| 2009/0076361 A1 | 3/2009 | Kamath et al. |
| 2009/0082693 A1 | 3/2009 | Stafford |
| 2009/0085768 A1 | 4/2009 | Patel et al. |
| 2009/0099436 A1 | 4/2009 | Brister et al. |
| 2009/0105554 A1 | 4/2009 | Stahmann et al. |
| 2009/0105560 A1 | 4/2009 | Solomon |
| 2009/0105570 A1 | 4/2009 | Sloan et al. |
| 2009/0105636 A1 | 4/2009 | Hayter et al. |
| 2009/0112478 A1 | 4/2009 | Mueller, Jr. et al. |
| 2009/0118589 A1 | 5/2009 | Ueshima et al. |
| 2009/0124877 A1 | 5/2009 | Goode, Jr. et al. |
| 2009/0124878 A1 | 5/2009 | Goode et al. |
| 2009/0124879 A1 | 5/2009 | Brister et al. |
| 2009/0124964 A1 | 5/2009 | Leach et al. |
| 2009/0131768 A1 | 5/2009 | Simpson et al. |
| 2009/0131769 A1 | 5/2009 | Leach et al. |
| 2009/0131776 A1 | 5/2009 | Simpson et al. |
| 2009/0131777 A1 | 5/2009 | Simpson et al. |
| 2009/0137886 A1 | 5/2009 | Shariati et al. |
| 2009/0137887 A1 | 5/2009 | Shariati et al. |
| 2009/0143659 A1 | 6/2009 | Li et al. |
| 2009/0143660 A1 | 6/2009 | Brister et al. |
| 2009/0143725 A1 | 6/2009 | Peyser et al. |
| 2009/0150186 A1 | 6/2009 | Cohen et al. |
| 2009/0156919 A1 | 6/2009 | Brister et al. |
| 2009/0156924 A1 | 6/2009 | Shariati et al. |
| 2009/0163790 A1 | 6/2009 | Brister et al. |
| 2009/0163791 A1 | 6/2009 | Brister et al. |
| 2009/0163855 A1 | 6/2009 | Shin et al. |
| 2009/0164190 A1 | 6/2009 | Hayter |
| 2009/0164239 A1 | 6/2009 | Hayter et al. |
| 2009/0164251 A1 | 6/2009 | Hayter |
| 2009/0173708 A1 | 7/2009 | Demiany et al. |
| 2009/0178459 A1 | 7/2009 | Li et al. |
| 2009/0182217 A1 | 7/2009 | Li et al. |
| 2009/0182517 A1 | 7/2009 | Gandhi et al. |
| 2009/0189738 A1 | 7/2009 | Hermle |
| 2009/0192366 A1 | 7/2009 | Mensinger et al. |
| 2009/0192380 A1 | 7/2009 | Shariati et al. |
| 2009/0192722 A1 | 7/2009 | Shariati et al. |
| 2009/0192724 A1 | 7/2009 | Brauker et al. |
| 2009/0192745 A1 | 7/2009 | Kamath et al. |
| 2009/0192751 A1 | 7/2009 | Kamath et al. |
| 2009/0198118 A1 | 8/2009 | Hayter et al. |
| 2009/0203981 A1 | 8/2009 | Brauker et al. |
| 2009/0204341 A1 | 8/2009 | Brauker et al. |
| 2009/0216103 A1 | 8/2009 | Brister et al. |
| 2009/0234200 A1 | 9/2009 | Husheer |
| 2009/0240120 A1 | 9/2009 | Mensinger et al. |
| 2009/0240128 A1 | 9/2009 | Mensinger et al. |
| 2009/0240193 A1 | 9/2009 | Mensinger et al. |
| 2009/0242399 A1 | 10/2009 | Kamath et al. |
| 2009/0242425 A1 | 10/2009 | Kamath et al. |
| 2009/0247855 A1 | 10/2009 | Boock et al. |
| 2009/0247856 A1 | 10/2009 | Boock et al. |
| 2009/0247857 A1 | 10/2009 | Harper et al. |
| 2009/0253973 A1 | 10/2009 | Bashan et al. |
| 2009/0267765 A1 | 10/2009 | Greene et al. |
| 2009/0287073 A1 | 11/2009 | Boock et al. |
| 2009/0287074 A1 | 11/2009 | Shults et al. |
| 2009/0289796 A1 | 11/2009 | Blumberg |
| 2009/0291634 A1 | 11/2009 | Saarisalo |
| 2009/0294277 A1 | 12/2009 | Thomas et al. |
| 2009/0299155 A1 | 12/2009 | Yang et al. |
| 2009/0299156 A1 | 12/2009 | Simpson et al. |
| 2009/0299162 A1 | 12/2009 | Brauker et al. |
| 2009/0299276 A1 | 12/2009 | Brauker et al. |
| 2010/0010324 A1 | 1/2010 | Brauker et al. |
| 2010/0010331 A1 | 1/2010 | Brauker et al. |
| 2010/0010332 A1 | 1/2010 | Brauker et al. |
| 2010/0057040 A1 | 3/2010 | Hayter |
| 2010/0057041 A1 | 3/2010 | Hayter |
| 2010/0057042 A1 | 3/2010 | Hayter |
| 2010/0057044 A1 | 3/2010 | Hayter |
| 2010/0057057 A1 | 3/2010 | Hayter et al. |
| 2010/0063372 A1 | 3/2010 | Potts et al. |
| 2010/0081906 A1 | 4/2010 | Hayter et al. |
| 2010/0081909 A1 | 4/2010 | Budiman et al. |
| 2010/0081953 A1 | 4/2010 | Syeda-Mahmood et al. |
| 2010/0121167 A1 | 5/2010 | McGarraugh et al. |
| 2010/0141656 A1 | 6/2010 | Krieftewirth |
| 2010/0160759 A1 | 6/2010 | Celentano et al. |
| 2010/0160761 A1 | 6/2010 | Say et al. |
| 2010/0168538 A1 | 7/2010 | Keenan et al. |
| 2010/0168546 A1 | 7/2010 | Kamath et al. |
| 2010/0174266 A1 | 7/2010 | Estes |
| 2010/0190435 A1 | 7/2010 | Cook et al. |
| 2010/0191085 A1 | 7/2010 | Budiman |
| 2010/0191472 A1 | 7/2010 | Doniger et al. |
| 2010/0198034 A1 | 8/2010 | Thomas et al. |
| 2010/0198142 A1 | 8/2010 | Sloan et al. |
| 2010/0204557 A1 | 8/2010 | Kiaie et al. |
| 2010/0213057 A1 | 8/2010 | Feldman et al. |
| 2010/0230285 A1 | 9/2010 | Hoss et al. |
| 2010/0234710 A1 | 9/2010 | Budiman et al. |
| 2010/0265073 A1 | 10/2010 | Harper et al. |
| 2010/0274515 A1 | 10/2010 | Hoss et al. |
| 2010/0277342 A1 | 11/2010 | Sicurello et al. |
| 2010/0280441 A1 | 11/2010 | Willinska et al. |
| 2010/0280782 A1 | 11/2010 | Harper et al. |
| 2010/0312176 A1 | 12/2010 | Lauer et al. |
| 2010/0313105 A1 | 12/2010 | Nekoomaram et al. |
| 2010/0317952 A1 | 12/2010 | Budiman et al. |
| 2010/0324392 A1 | 12/2010 | Yee et al. |
| 2010/0326842 A1 | 12/2010 | Mazza et al. |
| 2011/0002223 A1 | 1/2011 | Gross |
| 2011/0004276 A1 | 1/2011 | Blair et al. |
| 2011/0021889 A1 | 1/2011 | Hoss et al. |
| 2011/0024043 A1 | 2/2011 | Boock et al. |
| 2011/0024307 A1 | 2/2011 | Simpson et al. |
| 2011/0027127 A1 | 2/2011 | Simpson et al. |
| 2011/0027453 A1 | 2/2011 | Boock et al. |
| 2011/0027458 A1 | 2/2011 | Boock et al. |
| 2011/0028815 A1 | 2/2011 | Simpson et al. |
| 2011/0028816 A1 | 2/2011 | Simpson et al. |
| 2011/0029247 A1 | 2/2011 | Kalathil |
| 2011/0040163 A1 | 2/2011 | Telson et al. |
| 2011/0058485 A1 | 3/2011 | Sloan |
| 2011/0060530 A1 | 3/2011 | Fennell |
| 2011/0077490 A1 | 3/2011 | Simpson et al. |
| 2011/0077494 A1 | 3/2011 | Doniger et al. |
| 2011/0081726 A1 | 4/2011 | Berman et al. |
| 2011/0082484 A1 | 4/2011 | Saravia et al. |
| 2011/0105873 A1 | 5/2011 | Feldman et al. |
| 2011/0106126 A1 | 5/2011 | Love et al. |
| 2011/0112696 A1 | 5/2011 | Yodfat et al. |
| 2011/0148905 A1 | 6/2011 | Simmons et al. |
| 2011/0152637 A1 | 6/2011 | Kateraas et al. |
| 2011/0184268 A1 | 7/2011 | Taub |
| 2011/0190603 A1 | 8/2011 | Stafford |
| 2011/0191044 A1 | 8/2011 | Stafford |
| 2011/0193704 A1 | 8/2011 | Harper et al. |
| 2011/0208027 A1 | 8/2011 | Wagner et al. |
| 2011/0208155 A1 | 8/2011 | Palerm et al. |
| 2011/0210830 A1 | 9/2011 | Talty et al. |
| 2011/0213225 A1 | 9/2011 | Bernstein et al. |
| 2011/0224523 A1 | 9/2011 | Budiman |
| 2011/0257495 A1 | 10/2011 | Hoss et al. |
| 2011/0257895 A1 | 10/2011 | Brauker et al. |
| 2011/0263958 A1 | 10/2011 | Brauker et al. |
| 2011/0288574 A1 | 11/2011 | Curry et al. |
| 2011/0319729 A1 | 12/2011 | Donnay et al. |

(56) References Cited

U.S. PATENT DOCUMENTS

| | | |
|---|---|---|
| 2011/0320130 A1 | 12/2011 | Valdes et al. |
| 2011/0320167 A1 | 12/2011 | Budiman |
| 2012/0010642 A1 | 1/2012 | Lee et al. |
| 2012/0078071 A1 | 3/2012 | Bohm et al. |
| 2012/0084053 A1 | 4/2012 | Yuen et al. |
| 2012/0108931 A1 | 5/2012 | Taub |
| 2012/0108934 A1 | 5/2012 | Valdes et al. |
| 2012/0165626 A1 | 6/2012 | Irina et al. |
| 2012/0165640 A1 | 6/2012 | Galley et al. |
| 2012/0173200 A1 | 7/2012 | Breton et al. |
| 2012/0209099 A1 | 8/2012 | Ljuhs et al. |
| 2012/0215462 A1 | 8/2012 | Goode et al. |
| 2012/0233679 A1 | 9/2012 | Shedrinsky |
| 2012/0238851 A1 | 9/2012 | Kamen et al. |
| 2012/0245447 A1 | 9/2012 | Karan et al. |
| 2012/0255875 A1 | 10/2012 | Vicente et al. |
| 2012/0309302 A1 | 12/2012 | Buhot |
| 2013/0035575 A1 | 2/2013 | Mayou et al. |
| 2013/0127627 A1 | 5/2013 | Hayter et al. |
| 2013/0184547 A1 | 7/2013 | Taub et al. |
| 2013/0268736 A1 | 10/2013 | Okamoto et al. |
| 2014/0121480 A1 | 5/2014 | Budiman et al. |
| 2014/0121488 A1 | 5/2014 | Budiman |
| 2014/0176338 A1 | 6/2014 | He et al. |
| 2014/0221966 A1 | 8/2014 | Buckingham et al. |
| 2015/0216456 A1 | 8/2015 | Budiman |
| 2016/0022221 A1 | 1/2016 | Ou et al. |
| 2019/0216373 A1 | 7/2019 | Harper |

FOREIGN PATENT DOCUMENTS

| | | |
|---|---|---|
| EP | 0127958 | 12/1984 |
| EP | 0320109 | 6/1989 |
| EP | 0353328 | 2/1990 |
| EP | 0390390 | 10/1990 |
| EP | 0396788 | 11/1990 |
| EP | 0472411 | 2/1992 |
| EP | 0286118 | 1/1995 |
| EP | 0867146 | 9/1998 |
| EP | 1048264 | 11/2000 |
| EP | 1419731 | 5/2004 |
| EP | 0939602 | 9/2004 |
| EP | 1850909 | 4/2010 |
| EP | 1677668 | 7/2010 |
| EP | 2 498 196 | 9/2012 |
| WO | WO 1996/025089 | 8/1996 |
| WO | WO 1996/035370 | 11/1996 |
| WO | WO 97/18639 | 5/1997 |
| WO | WO 1997/015227 | 5/1997 |
| WO | WO 99/58190 | 11/1999 |
| WO | WO 2000/049940 | 8/2000 |
| WO | WO 00/62664 A1 | 10/2000 |
| WO | WO 2000/059370 | 10/2000 |
| WO | WO 2000/074753 | 12/2000 |
| WO | WO 2001/052935 | 7/2001 |
| WO | WO 2001/054753 | 8/2001 |
| WO | WO 2002/016905 | 2/2002 |
| WO | WO 2003/076893 | 9/2003 |
| WO | WO 2003/082091 | 10/2003 |
| WO | WO 2004/060455 | 7/2004 |
| WO | WO 2005/065542 | 7/2005 |
| WO | WO 2006/024671 | 3/2006 |
| WO | WO 2006/081336 | 8/2006 |
| WO | WO 2006/085087 | 8/2006 |
| WO | WO 2007/097754 | 8/2007 |
| WO | WO 2008/001366 | 1/2008 |
| WO | WO 2008/086541 | 7/2008 |
| WO | WO 2008/157821 | 12/2008 |
| WO | WO 2013/019225 | 2/2013 |

OTHER PUBLICATIONS

U.S. Appl. No. 15/292,107, filed Aug. 13, 2020 Notice of Allowance.

U.S. Appl. No. 15/292,107, filed Jul. 20, 2020 Amendment and Request for Continued Examination (RCE).

U.S. Appl. No. 15/292,107, filed Apr. 22, 2020 Notice of Allowance.

U.S. Appl. No. 15/292,107, filed Apr. 10, 2020 Response after Final Action.

U.S. Appl. No. 15/292,107, filed Jan. 27, 2020 Final Office Action.

U.S. Appl. No. 15/292,107, filed Oct. 7, 2019 Response to Non-Final Office Action.

U.S. Appl. No. 15/292,107, filed May 31, 2019 Non-Final Office Action.

Armour, J. C., et al., "Application of Chronic Intravascular Blood Glucose Sensor in Dogs", Diabetes, vol. 39, 1990, pp. 1519-1526.

Arnold, M. A., et al., "Selectivity Assessment of Noninvasive Glucose Measurements Based on Analysis of Multivariate Calibration Vectors", Journal of Diabetes Science and Technology, vol. 1, No. 4, 2007, pp. 454-462.

Bennion, N., et al., "Alternate Site Glucose Testing: A Crossover Design", Diabetes Technology & Therapeutics, vol. 4, No. 1, 2002, pp. 25-33.

Blank, T. B., et al., "Clinical Results From a Non-Invasive Blood Glucose Monitor", Optical Diagnostics and Sensing of Biological Fluids and Glucose and Cholesterol Monitoring II, Proceedings of SPIE, vol. 4624, 2002, pp. 1-10.

Boyne, M. S., et al., "Timing of Changes in Interstitial and Venous Blood Glucose Measured With a Continuous Subcutaneous Glucose Sensor", Diabetes, vol. 52, Nov. 2003, pp. 2790-2794.

Bremer, T. M., et al., "Benchmark Data from the Literature for Evaluation of New Glucose Sensing Technologies", Diabetes Technology & Therapeutics, vol. 3, No. 3, 2001, pp. 409-418.

Brooks, S. L., et al., "Development of an On-Line Glucose Sensor for Fermentation Monitoring", Biosensors, vol. 3, 1987/1988, pp. 45-56.

Cass, A. E., et al., "Ferrocene-Medicated Enzyme Electrode for Amperometric Determination of Glucose", Analytical Chemistry, vol. 56, No. 4, 1984, 667-671.

Cheyne, E. H., et al., "Performance of a Continuous Glucose Monitoring System During Controlled Hypoglycaemia in Healthy Volunteers", Diabetes Technology & Therapeutics, vol. 4, No. 5, 2002, pp. 607-613.

Choleau, C., et al., "Calibration of a Subcutaneous Amperometric Glucose Sensor Implanted for 7 Days in Diabetic Patients Part 2. Superiority of the One-Point Calibration Method", Biosensors and Bioelectronics, vol. 17, No. 8, 2002, pp. 647-654.

Csoregi, E., et al., "Design and Optimization of a Selective Subcutaneously Implantable Glucose Electrode Based on 'Wired' Glucose Oxidase", Analytical Chemistry, vol. 67, No. 7, 1995, pp. 1240-1244.

Diabetes Control and Complications Trial Research Group, "The Effect of Intensive Treatment of Diabetes on the Development and Progression of Long-Term Complications in Insulin-Dependent Diabetes Mellitus," New England J. Med. vol. 329, 1993, pp. 977-986.

Eren-Oruklu, M., et al., "Estimation of Future Glucose Concentrations with Subject-Specific Recursive Linear Models", Diabetes Technology & Therapeutics vol. 11(4), 2009, pp. 243-253.

Feldman, B., et al., "A Continuous Glucose Sensor Based on Wired EnzymeTM Technology—Results from a 3-Day Trial in Patients with Type 1 Diabetes", Diabetes Technology & Therapeutics, vol. 5, No. 5, 2003, pp. 769-779.

Feldman, B., et al., "Correlation of Glucose Concentrations in Interstitial Fluid and Venous Blood During Periods of Rapid Glucose Change", Abbott Diabetes Care, Inc. Freestyle Navigator Continuous Glucose Monitor Pamphlet, 2004.

Georgescu, B., et al., "Real-Time Multimodel Tracking of Myocardium in Echocardiography Using Robust Information Fusion", Medical Image Computing and Computer-Assisted Intervention, 2004, pp. 777-785.

Goldman, J. M., et al., "Masimo Signal Extraction Pulse Oximetry", Journal of Clinical Monitoring and Computing, vol. 16, No. 7, 2000, pp. 475-483.

(56) References Cited

OTHER PUBLICATIONS

Guerci, B., et al., "Clinical Performance of CGMS in Type 1 Diabetic Patients Treated by Continuous Subcutaneous Insulin Infusion Using Insulin Analogs", Diabetes Care, vol. 26, 2003, pp. 582-589.

Isermann, R., "Supervision, Fault-Detection and Fault-Diagnosis Methods—An Introduction", Control Engineering Practice, vol. 5, No. 5, 1997, pp. 639-652.

Isermann, R., et al., "Trends in the Application of Model-Based Fault Detection and Diagnosis of Technical Processes", Control Engineering Practice, vol. 5, No. 5, 1997, pp. 709-719.

Johnson, P. C., "Peripheral Circulation", John Wiley & Sons, 1978, pp. 198.

Jungheim, K., et al., "How Rapid Does Glucose Concentration Change in Daily Life of Patients with Type 1 Diabetes?", 2002, pp. 250.

Jungheim, K., et al., "Risky Delay of Hypoglycemia Detection by Glucose Monitoring at the Arm", Diabetes Care, vol. 24, No. 7, 2001, pp. 1303-1304.

Kaplan, S. M., "Wiley Electrical and Electronics Engineering Dictionary", IEEE Press, 2004, pp. 141, 142, 548, 549.

Kovatchev, B. P., et al., "Evaluating the Accuracy of Continuous Glucose-Monitoring Sensors", Diabetes Care, vol. 27, No. 8, 2004, pp. 1922-1928.

Kuure-Kinsey, M., et al., "A Dual-Rate Kalman Filter for Continuous Glucose Monitoring", Proceedings of the 28th IEEE, EMBS Annual International Conference, New York City, 2006, pp. 63-66.

Lodwig, V., et al., "Continuous Glucose Monitoring with Glucose Sensors: Calibration and Assessment Criteria", Diabetes Technology & Therapeutics, vol. 5, No. 4, 2003, pp. 573-587.

Lortz, J., et al., "What is Bluetooth? We Explain The Newest Short-Range Connectivity Technology", Smart Computing Learning Series, Wireless Computing, vol. 8, Issue 5, 2002, pp. 72-74.

Maher, "A Method for Extrapolation of Missing Digital Audio Data", Preprints of Papers Presented at the AES Convention, 1993, pp. 1-19.

Maher, "Audio Enhancement using Nonlinear Time-Frequency Filtering", AES 26$^{th}$ International Conference, 2005, pp. 1-9.

Malin, S. F., et al., "Noninvasive Prediction of Glucose by Near-Infrared Diffuse Reflectance Spectoscopy", Clinical Chemistry, vol. 45, No. 9, 1999, pp. 1651-1658.

Mcgarraugh, G., et al., "Glucose Measurements Using Blood Extracted from the Forearm and the Finger", TheraSense, Inc., 2001, 16 Pages.

Mcgarraugh, G., et al., "Physiological Influences on Off-Finger Glucose Testing", Diabetes Technology & Therapeutics, vol. 3, No. 3, 2001, pp. 367-376.

Mckean, B. D., et al., "A Telemetry-Instrumentation System for Chronically Implanted Glucose and Oxygen Sensors", IEEE Transactions on Biomedical Engineering, vol. 35, No. 7, 1988, pp. 526-532.

Morbiducci, U, et al., "Improved Usability of the Minimal Model of Insulin Sensitivity Based on an Automated Approach and Genetic Algorithms for Parameter Estimation", Clinical Science, vol. 112, 2007, pp. 257-263.

Mougiakakou, et al., "A Real Time Simulation Model of Glucose-Insulin Metabolism for Type 1 Diabetes Patients", Proceedings of the 2005 IEEE, 2005, pp. 298-301.

Panteleon, A. E., et al., "The Role of the Independent Variable to Glucose Sensor Calibration", Diabetes Technology & Therapeutics, vol. 5, No. 3, 2003, pp. 401-410.

Parker, R., et al., "Robust H∞ Glucose Control in Diabetes Using a Physiological Model", AIChE Journal, vol. 46, No. 12, 2000, pp. 2537-2549.

Pickup, J., et al., "Implantable Glucose Sensors: Choosing the Appropriate Sensing Strategy", Biosensors, vol. 3, 1987/1988, pp. 335-346.

Pickup, J., et al., "In Vivo Molecular Sensing in Diabetes Mellitus: An Implantable Glucose Sensor with Direct Electron Transfer", Diabetologia, vol. 32, 1989, pp. 213-217.

Pishko, M. V., et al., "Amperometric Glucose Microelectrodes Prepared Through Immobilization of Glucose Oxidase in Redox Hydrogels", Analytical Chemistry, vol. 63, No. 20, 1991, pp. 2268-2272.

Quinn, C. P., et al., "Kinetics of Glucose Delivery to Subcutaneous Tissue in Rats Measured with 0.3-mm Amperometric Microsensors", The American Physiological Society, 1995, E155-E161.

Roe, J. N., et al., "Bloodless Glucose Measurements", Critical Review in Therapeutic Drug Carrier Systems, vol. 15, Issue 3, 1998, pp. 199-241.

Sakakida, M., et al., "Development of Ferrocene-Mediated Needle-Type Glucose Sensor as a Measure of True Subcutaneous Tissue Glucose Concentrations", Artificial Organs Today, vol. 2, No. 2, 1992, pp. 145-158.

Sakakida, M., et al., "Ferrocene-Mediated Needle-Type Glucose Sensor Covered with Newly Designed Biocompatible Membrane", Sensors and Actuators B, vol. 13-14, 1993, pp. 319-322.

Salehi, C., et al., "A Telemetry-Instrumentation System for Long-Term Implantable Glucose and Oxygen Sensors", Analytical Letters, vol. 29, No. 13, 1996, pp. 2289-2308.

Schmidtke, D. W., et al., "Measurement and Modeling of the Transient Difference Between Blood and Subcutaneous Glucose Concentrations in the Rat After Injection of Insulin", Proceedings of the National Academy of Sciences, vol. 95, 1998, pp. 294-299.

Shaw, G. W., et al., "In Vitro Testing of a Simply Constructed, Highly Stable Glucose Sensor Suitable for Implantation in Diabetic Patients", Biosensors & Bioelectronics, vol. 6, 1991, pp. 401-406.

Shichiri, M., et al., "Glycaemic Control in Pancreatectomized Dogs with a Wearable Artificial Endocrine Pancreas", Diabetologia, vol. 24, 1983, pp. 179-184.

Shichiri, M., et al., "In Vivo Characteristics of Needle-Type Glucose Sensor—Measurements of Subcutaneous Glucose Concentrations in Human Volunteers", Hormone and Metabolic Research Supplement Series, vol. 20, 1988, pp. 17-20.

Shichiri, M., et al., "Membrane Design for Extending the Long-Life of an Implantable Glucose Sensor", Diabetes Nutrition and Metabolism, vol. 2, 1989, pp. 309-313.

Shichiri, M., et al., "Needle-type Glucose Sensor for Wearable Artificial Endocrine Pancreas", Implantable Sensors for Closed-Loop Prosthetic Systems, Chapter 15, 1985, pp. 197-210.

Shichiri, M., et al., "Telemetry Glucose Monitoring Device With Needle-Type Glucose Sensor: A Useful Tool for Blood Glucose Monitoring in Diabetic Individuals", Diabetes Care, vol. 9, No. 3, 1986, pp. 298-301.

Shichiri, M., et al., "Wearable Artificial Endocrine Pancreas With Needle-Type Glucose Sensor", The Lancet, 1982, pp. 1129-1131.

Shults, M. C., et al., "A Telemetry-Instrumentation System for Monitoring Multiple Subcutaneously Implanted Glucose Sensors", IEEE Transactions on Biomedical Engineering, vol. 41, No. 10, 1994, pp. 937-942.

Sternberg, R., et al., "Study and Development of Multilayer Needle-Type Enzyme-Based Glucose Microsensors", Biosensors, vol. 4, 1988, pp. 27-40.

Thompson, M., et al., "In Vivo Probes: Problems and Perspectives", Clinical Biochemistry, vol. 19, 1986, pp. 255-261.

Turner, A., et al., "Diabetes Mellitus: Biosensors for Research and Management", Biosensors, vol. 1, 1985, pp. 85-115.

Updike, S. J., et al., "Principles of Long-Term Fully Implanted Sensors with Emphasis on Radiotelemetric Monitoring of Blood Glucose from Inside a Subcutaneous Foreign Body Capsule (FBC)", Biosensors in the Body: Continuous in vivo Monitoring, Chapter 4, 1997, pp. 117-137.

Velho, G., et al., "Strategies for Calibrating a Subcutaneous Glucose Sensor", Biomedica Biochimica Acta, vol. 48, 1989, pp. 957-964.

Whipple, G., "Low Residual Noise Speech Enhancement Utilizing Time-Frequency", Proceedings of the International Conference on Acoustics, Speech, and Signal Processing, vol. 19, 1994, pp. I5-I8.

Wilson, G. S., et al., "Progress Toward the Development of an Implantable Sensor for Glucose", Clinical Chemistry, vol. 38, No. 9, 1992, pp. 1613-1617.

(56) References Cited

OTHER PUBLICATIONS

Wolfe, P. J., et al., "Interpolation of Missing Data Values for Audio Signal Restoration Using a Gabor Regression Model", 2005 IEEE International Conference on Acoustics, Speech, and Signal Processing, vol. 5, 2005, pp. 517-520.
U.S. Appl. No. 14/210,330, Notice of Allowance dated Sep. 14, 2016.
U.S. Appl. No. 14/210,330, Office Action dated Feb. 8, 2016.
U.S. Appl. No. 14/210,330, Office Action dated Jun. 17, 2016.
"In Vivo Glucose Sensing", Chemical Analysis, A Series of Monographs on Analytical Chemistry and its Applications, vol. 174, 62 pages (2010).
Decuir, "Bluetooth 4.0:Low Energy", Standards Architect, CSR Technology, Councilor, Bluetooth Architecture Review Board, IEEE Region 6 Northwest Area Chair, 104 pages (2012).
Dementyev, et al., "Power Consumption Analysis of Bluetooth Low Energy, ZigBee and ANT Sensor Nodes in a Cyclic Sleep Scenario", IEEE International Wireless Symposium (IWS), 5 pages (2013).
Guardian® REAL-Time Continuous Glucose Monitoring System User Guide, Medtronic MiniMed, 181 pages (2006).
Klonoff, "A Review of Continuous Glucose Monitoring Technology", Diabetes Technology & Therapeutics, 7(5):770-775 (2005).
Klonoff, "Continuous Glucose Monitoring: Roadmap for 21st century diabetes therapy", Diabetes Care, 28(5):1231-1239 (2005).
Morak, et al., "Design and Evaluation of a Telemonitoring Concept Based on NFC-Enabled Mobile Phones and Sensor Devices", IEEE Transactions on Information Technology in Biomedicine, 16(1):17-23 (2012).
Movassaghi, et al., "Wireless Technologies for Body Area Networks: Characteristics and Challenges", IEEE, International Symposium on Communications and Information Technologies (ISCIT), pp. 42-47 (2012).
Specification of the Bluetooth System, Experience More, Specification vol. 0, Covered Core Package Version: 4.0, 2302 pages (2010).
Townsend, et al., "Getting Started with Bluetooth Low Energy [Book]", O'Reilly, retrieved from https://www.oreilly.com/library/view/getting-started-with/9781491900550/ch01.html on May 5, 2020, 26 pages.
Wikipedia, "Blood glucose monitoring" retrieved from "https://web.archive.org/web/20111215063153/http://en.wikipedia.org/wiki/Blood_glucose_monitoring" on Aug. 1, 2021, 6 pages.
Wikipedia, "Near field communication" retrieved from "http://en.wikipedia.org/w/index.php?title=Near_field_communication&oldid=543740757" on Jun. 27, 2014, 14 pages.
CareLink™ Usb, User Guide Medtronic MiniMed, 11pages (2007).
Guardian® RT, Continuous Glucose Monitoring System, REF MMT-7900, User Guide, Medtronic MiniMed, 128 pages (2005).
Ocean Systems Test and Evaluation Program, Data Communications Plan, NOAA, U.S. Department of Commerce, National Ocean Service Center for Operational Oceanographic Products and Services, 199 pages, May 2006.
The MiniMed Paradigm REAL-Time System: A Practical Guide to Continuous Glucose Monitoring, 18 pages (2006).
The MiniMed Paradigm REAL-Time Insulin Pump and Continuous Glucose Monitoring System, Fact Sheet, 2 pages (2006).
The MiniMed Paradigm REAL-Time Insulin Pump and Continuous Glucose Monitoring System, 522 and 722 Insulin Pumps User Guide, 262 pages (2008).
"Abbott Receives CE Mark for Freestyle®Libre, A Revolutionary Glucose Monitoring System for People with Diabetes," 8 pages (2023).
Armstrong, "Wireless connectivity for health and sports monitoring: a review," Br J Sports Med, 41:285-289 (2007).
ATTD Program, 4 pages (2009).
Boise, Interview with Dexcom CEO, Dexcom CEO Kevin Sayer Explains G6, 9 pages (2018).
Breton et al., "Optimum Subcutaneous Glucose Sampling and Fourier," Journal of Diabetes Science and Technology, vol. 2, Issue 3, 495-500, May 2008.

Buckingman et al., "Real-time subcutaneous glucose monitoring," Curr Opinion Endorinology, Diabetes & Obesity, 14:288-295 (2007).
Buckingman et al., "Clinical Overview of Continuous Glucose Monitoring," Journal of Diabetes Science and Technology, vol. 2, Issue 2, 300-306 (2008).
Burge et al., "Continuous Glucose Monitoring: The Future of Diabetes Management," Diabetes Spectrum, vol. 21, No. 2, 112-119 (2008).
Choleua et al., "Calibration of a subcutaneous amperometric glucose sensor implanted for 7 days in diabetic patients Part 2. Superiority of the one-point calibration method," Biosensors and Bioelectronics 17, 647-654 (2002).
Dexcom (DXCM) Company Profile, 2017 / Q4 Earnings call transcript, 12 pages (2017).
Dexcp, G6 Continuous Glucose Monitoring System User Guide, 7 pages (2020).
Email communication from Sophie Hood, Jan. 24, 2023, 6 pages.
Excerpts from Diabetes Forecast, 18 pages, Nov. 2007.
Excerpts F. White Affidavit, Medtronic MiniMed, Inc., Questions regarding MiniMed Paradigm, 94 pages (2007).
Excerpts F. White Affidavit, Medtronic MiniMed, Inc., MiniMed User Guides, 11 pages (2007).
FDA, Premarket Approval (PMA), 3 pages, Apr. 7, 2006.
File History, U.S. Appl. No. 9/935,827, 97 pages, filed Aug. 23, 2001.
File History, U.S. Appl. No. 10/335,256, 103 pages, filed Dec. 31, 2002.
File History, U.S. Appl. No. 11/322,568, 94 pages, filed Dec. 30, 2005.
File History, U.S. Appl. No. 11/931,363, 72 pages, filed Oct. 31, 2007.
File History, U.S. Appl. No. 12/056,651, 323 pages, filed Mar. 27, 2008.
File History, U.S. Appl. No. 12/769,635, 280 pages, filed Apr. 28, 2010.
File History, U.S. Appl. No. 13/925,694, 214 pages, filed Jun. 24, 2013.
File History, U.S. Appl. No. 15/061,774, 151 pages, filed Mar. 4, 2016.
File History, U.S. Appl. No. 16/228,910, 212 pages, filed Dec. 21, 2018.
File History, U.S. Appl. No. 17/245,719, 168 pages, filed Mar. 30, 2021.
File History, U.S. Appl. No. 17/411,154, 320 pages, filed Aug. 25, 2021.
Hall, Interview with Kevin Sayer, President and CEO of Dexcom About The New Dexcom G6, College Diabetes Network, 6 pages (2021).
Heller et al., "Electrochemical Glucose Sensors and Their Applications in Diabetes Management," Chem. Rev, 108, 2482-2505 (2008).
Hoss et al., "Continuous glucose monitoring in the tissue: Do we really need to calibrate in-vivo?," Diabetes Technology & Therapeutics, vol. 11, No. 2, (2009).
Keenan et al., "Delays in Minimally Continuous Glucose Monitoring Devices: A Review of Current Technology," J Diabetes Sci Technol, vol. 3, Issue 5, 1207-1214 (2009).
Mastrototaro, "The MiniMed Continuous Glucouse Monitoring System," Diabetes Technology & Therapeutics, vol. 2, Suppl. 1, S-13-S-18 (2000).
McGarraugh, "The Chemistry of Commercial Continuous Glucouse Monitors," Technology & Theraputics, vol. 11, Suppl. 1, S-17-S-24 (2009).
Omnipod image, Exhibit 182, 2 pages, (Sep. 22, 2022).
News Release, "Medtronic Receives FDA Approval for World's First Insulin Pump with Real-Time Continuous Glucose Monitoring -- MiniMed Paradigm® REAL-Time System Allows Patients to Make Immediate Diabetes Management Decisions; Marks Major Step Toward an Artificial Pancreas," The Wayback Machine—https://web.archive.org/web/2006042708443 1/http://wwwp.medtronic.com:80/Newsroom/NewsReleaseDetails.do?itemId=114487, 2 pages (2006).

(56) References Cited

OTHER PUBLICATIONS

Pantelopoulos et al., "A Survey on Wearable Biosensor Systems for Health Monitoring," 30th Annual International IEEE EMBS Conference, Vancouver, British Columbia, Canada, Aug. 20-24, 2008, 4887-4890 (2018).
Poitout et al., "A glucose monitoring system for on line estimation in man of blood glucose concentration using a miniaturized glucose sensor implanted in the subcutaneous tissue and a wearable control unit," Diabetologia, 36: 658-663 (1993).
Ruder, "Continuous Glucose Monitors For Kids," Diabetes Forecast, 1 page, Aug. 2007.
Sayer, CGMS Changing Diabetes Management: Kevin Sayer, DIC Interview Transcript, Featuring Steve Freed, 11 pages (2019).
Shenoi, "Introduction to Digital Signal Processing and Filter Design," Wiley & Sons, 46 pages (2006).
S&P Global Market Intelligence "DexCom, Inc. NasdaqGS:DXCM, Company Conference Presentation," 17 pages (2021).
S&P Global Market Intelligence "DexCom, Inc. NasdaqGS:DXCM, Company Conference Presentation," 10 pages (2020).
S&P Global Market Intelligence "DexCom, Inc. NasdaqGS:DXCM, Company Conference Presentation," 11 pages (2019).
Smith, The Science and Engineer's Guide to Digital Signal Processing, $2^{nd}$ Ed., 46 pages (1999).
U.S. Appl. No. 10/335,256 Specification and Drawings for "Relay device for transferring information between a sensor system and a fluid delivery system," filed Dec. 31, 2002, 88 pages.
U.S. Appl. No. 11/322,568 Specification and Drawings for "Telemetered characteristic monitor system and method of using the same," filed Dec. 30, 2005, 50 pages.
Sonix, Dexcom CEO- Prime Position in Our Market—Mad Money—CNBC.mp4, 4 pages.
U.S. Food & Drug Administration, "Deciding When to Submit a 510(k) for a Change to an Existing Device, Guidance for Industry and Food and Drug Administration Staff," 78 pages (2017).
U.S. Food & Drug Administration, "Deciding When to Submit a 510(k) for a Change to an Existing Device, Guidance for Industry and Food and Drug Administration Staff," 32 pages (2017).
U.S. Appl. No. 17/245,719, filed Apr. 30, 2021, 51 pages.
U.S. Appl. No. 16/228,910, filed Dec. 21, 2018, 37 pages.
U.S. Appl. No. 60/976,886, filed Oct. 2, 2007, 62 pages.
Velho et al., "In vivo calibration of a subcutaneous glucose sensor for determination of subcutaneous glucose kinetics," Diabetes, American Diabetes Assocation, 1 (3), pp. 227-233. hal-1179359 (1988).
Watkin, "An Introduction to Flash Glucose Monitoring," 16 pages (2013).
U.S. Appl. No. 60/614,683, filed Sep. 30, 2004, Brister, et al..
"Within Definition & Meaning" retrieved from "https://www.dictionary.com/browse/within" on Sep. 9, 2022, 5 pages.
Bluetooth, Bluetooth Basics, Benefits of Bluetooth Technology, https://web.archive.org/web/20060611161103/http://www.bluetooth.com/Bluetooth/Learn/Basics/, 2006, 1 page.
Breton, et al., "Optimum Subcutaneous Glucose Sampling and Fourier Analysis of Continuous Glucose Monitors", Journal of Diabetes Science and Technology, 2(3):495- 500 (2008).
Declaration of Brian D. Gross, 150 pages (2023).
Declaration of Morten O. Jensen, Ph.D., Dr.Med, 67 pages (2023).
Declaration of Nathaniel E. Frank-White, Nov. 9, 2023, 28 pages.
Defendant's Answering Claim Construction Brief, Abbott Diabetes v. Dexcom, Inc., Aug. 3, 2022, 59 pages.
Dexcom Continuous Glucose Monitoring, Discover Dexcom G5 Mobile Continuous Glucose Monitoring (CGM) System, CGM unveils what no meter can . . . , Oct. 17, 2023, 18 pages.
Dexcom Continuous Glucose Monitoring, FDA Approves Dexcom G5® Mobile Continuous Glucose Monitoring System, Aug. 24, 2015, 6 pages.
Dexcom G4 Platinum Pediatric, User's Guide Dexcom G4® Platinum (Pediatric) Continuous Glucose Monitoring System Received with ShareTM, 2015, 234 pages.
Dexcom, Inserting Sensor, Instructions for Use, Dexcom, Inc., 2 pages (2021).
Dexcomg7, Operational Manual, User Guide, Dexcom, Inc., 179 pages (2022) (with an English abstract).
Dexcomg7, Receiver: Start Here, Operational Manual, Dexcom, Inc., 8 pages (2022).
Dexcomg7, Start Here, Operational Manual, Dexcom, Inc. 9 pages (2022) (with an English abstract).
FDA U.S. Food & Drug Administration, Premarket Approval (PMA), Sep. 16, 2006, https://www.accessdata.fda.gov/scripts/cdrh/cfdocs/cfpma/pma.cfm?ID=388585, 4 pages.
Federal Communications Commission Office of Engineering and Technology Policy and Rules Division, FCC Online Table of Frequency Allocations, Revised on Jul. 1, 2022, 180 pages.
File Wrapper of U.S. Appl. No. 17/245,719, filed Apr. 30, 2021, 168 pages.
File Wrapper of U.S. Appl. No. 17/411,154 (Part 1) filed Aug. 25, 2021, 160 pages.
File Wrapper of U.S. Appl. No. 17/411,154 (Part 2) filed Aug. 25, 2021, 160 pages.
File Wrapper of U.S. Appl. No. 17/411,154, filed Aug. 25, 2021, 54 pages.
File Wrapper of U.S. Provisional U.S. Appl. No. 60/614,683, filed Sep. 30, 2004, 447 pages.
iPhone User Guide for iOS 8.4 Software, 2015, 196 pages.
Medtronic MiniMed, Inc., Fact Sheet, Features and Benefits for the MiniMed Paradigm REAL-Time System—https://web.archive.org/web/20071030065834/http://www.medtronicdiabetes.com/pdf/dtc_features_glance.pdf, 7 pages (2007) and Affidavit of Nathaniel E Frank-White, Internet Archive, 3 pages (2023).
Medtronic MiniMed, Inc., Features for the MiniMed Paradigm® REAL-Time System, The Wayback Machine—http://www.medtronicdiabetes.com/products/insulinpumps/features/index.html, 3 pages (2007) and Affidavit of Nathaniel E Frank-White, Internet Archive, 3 pages (2023).
Medtronic MiniMed, Inc., Frequently Asked Questions About the MiniMed Paradigm® REAL-Time System, The Wayback Machine—https://web.archive.org/web/20071023121607/http://www.medtronicdiabetes.com/products/insulinpumps/features/index.html, 9 pages (2007) and Affidavit of Nathaniel E Frank-White, Internet Archive, 3 pages (2023).
Medtronic MiniMed, Inc., Request Information for the MiniMed Paradigm® REAL-Time Insulin Pump and Continuous Glucose Monitoring System, The Wayback Machine—https://web.archive.org/web/20071009144413/http://www.medtronicdiabetes.com/index.html, 3 pages (2007) and Affidavit of Nathaniel E Frank-White, Internet Archive, 3 pages (2023).
Medtronic, CareLink Personal Therapy Management Software for Diabetes, 2007, 20 pages.
Memorandum Opinion, Abbott Diabetes v. Dexcom, Inc., Mar. 22, 2023, 47 pages.
Microchip, microID® 13.56 MHz RFID, System Design Guide, (2004), 214 pages.
Pantelopoulos, et al., "A Survey on Wearable Biosensor Systems for Health Monitoring", 2008 $30^{th}$ Annual International Conference of the IEEE Engineering in Medicine and Biology Society, Vancouver, British Columbia, Canada, pp. 4887-4890 (2008).
Seven STS® Continuous Glucose Monitoring System User's Guide, 2007, 74 pages.
The MiniMed Paradigm® Insulin Pump and Continuous Glucose Monitoring System, Sensor Features User Guide, Paradigm® 522 and 722 Sensor Features, Medtronic MiniMed, 76 pages (2006) and Affidavit of Nathaniel E Frank-White, Internet Archive, 3 pages (2023).
United States Patent and Trademark Office, Before the Patent Trial and Appeal Board, *Dexcom, Inc. v. Abbott Diabetes Care Inc.*, Petitioner's Explanation of Material Differences Between Petitions in U.S. Pat. No. 11,298,056 issued on Apr. 12, 2022, 8 pages (2023).
United States Patent and Trademark Office, Before the Patent Trial and Appeal Board, *Dexcom, Inc. v. Abbott Diabetes Care Inc.*, Petition for Inter Partes Review of U.S. Pat. No. 11,298,056 issued on Apr. 12, 2022, 132 pages (2023).

(56) References Cited

OTHER PUBLICATIONS

United States Patent and Trademark Office, Before the Patent Trial and Appeal Board, *Dexcom, Inc. v. Abbott Diabetes Care Inc.*, Notice of Filing Date Accorded to Petition and Time for Filing Patent Owner Preliminary Response in U.S. Pat. No. 11,298,056 issued on Apr. 12, 2022, 6 pages (2023).
United States Patent and Trademark Office, Before the Patent Trial and Appeal Board, *Dexcom, Inc. v. Abbott Diabetes Care Inc.*, Petition for Inter Partes Review of U.S. Pat. No. 11,298,056 issued on Apr. 12, 2022, 76 pages (2023).
FreeStyle Navigator Continuous Glucose Monitoring System, Dept of Health & Human Services, Food and Drug Administration, Mar. 12, 2008, 8 pages.
Almurashi, A.M., et al., "Emerging Diabetes Technologies: Continuous Glucose Monitors/ Artificial Pancreases" J. Indian Inst. Sci, 2023, 26 pages.
Atmel® 8-bit AVR® Microcontroller with 16K Bytes In-System Programmable Flash, Atmega169P, 2010, 395 pages.
Atmel® Product Guide, 2008, 90 pages.
Cappon, G., et al., "Continuous Glucose Monitoring Sensors for Diabetes Management: A Review of Technologies and Applications" Diabetes Metabolism Journal, 2019;43:383-397.
Certified U.S. Pat. No. 11,000,216, Issued May 11, 2021, 86 pages.
CGM Frustration Survey, Dexcom, 2020, 37 pages.
Clinical Trials Competitor and Ecosystem Players, Abbott, 2020, 29 pages.
Das, S.K., et al., "Review-Electrochemistry and Other Emerging Technologies for Continuous Glucose Monitoring Devices" ECS Sensors Plus, 2022, 19 pages.
Declaration of Karl R. Leinsng, MSME, PE, In Support of Abbott's Motion for Summary Judgement, 2023, 81 pages.
Dexcom G6 Continuous Glucose Monitoring System, User Guide, 2022, 346 pages.
Dexcom® User Guide for Dexcom G5® Mobile Continuous Glucose Monitoring (CGM) System, 2016, 372 pages.
DexcomTMSTSTM-7 Continuous Glucose Monitoring System, Transmitter model No. 9400-02, 2006, 3 pages.
FreeStyle Libre 2 HCP Pulse, Abbott, 2021, 14 pages.
FreeStyle Libre 3 Continuous Glucose Monitoring System, User's Manual, 2023, 248 pages.
FreeStyle Navigator® Continuous Glucose Monitoring System, User Guide, 2008, 196 pages.
Garg, S.K., et al., "Flash Glucose Monitoring: The Future is Here" Diabetes Technology & Therapeutics, vol. 19, Supplement 2, 2017, 3 pages.
Global Commercial Insights Meeting, Abbott, 2019, 69 pages.
Glucose Sensor Applicator, Project Status Update, design concept, Dexcom, 2014, 6 pages.
Hirsch, I.B, et al., "Role of Continuous Glucose Monitoring in Diabetes Treatment" American Diabetes Association, Abbott, 2018, 28 pages.
International Diabetes Device, 2022 Blue Book, Seagrove Partners, Globeview™M, 143 Pages.
National Diabetes Statistics Report, Estimates of Diabetes and Its Burden in the United States, 2023, 15 pages.
Seven®+Plus continuous glucose monitoring system, Users Guide, Dexcom, 2010, 144 pages.
The Minimed Paradigm® REAL-Time Insulin Pump and Continuous Glucose Monitoring System, Insulin Pump User Guide, Medtronic, 2007, 180 pages.
Armstrong, "Wireless connectivity for health and sports monitoring: a review," Br. J. Sports Med, 41:285-289 (2007)—8 pages Appendix F.
Breton et al., "Optimum Subcutaneous Glucose Sampling and Fourier Analysis of Continuous Glucose Monitors," Journal of Diabetes Science and Technology, vol. 2, Issue 3, 495-500 (May 2008).
Buckingham, "Clinical Overview of Continuous Glucose Monitoring," Journal of Diabetes Science and Technology, vol. 2, Issue 2, 300-306 (2008)—26 pages Appendix J.
Buckingham et al., "Real-time continuous glucose monitoring," Current Opinion in Endocrinology, Diabetes & Obesity, 288-295 (2007).
Buckingham et al., "Real-time continuous glucose monitoring," Current Opinion in Endocrinology, Diabetes & Obesity, 288-295 (2007)—20 pages Appendix I.
Diabetes Forecast, "Continuous Glucose Monitors for Kids," Practical Living, 1 page (Aug. 2007).
Diabetes Forecast, "Continuous Glucose Monitors for Kids," Practical Living, 10 pages (Aug. 2007).
Excerpts Diabetes Forecast, 18 pages (Nov. 2007).
File History of U.S. Pat. No. 11,013,431, issued May 25, 2021, 212 pages.
File History of U.S. Pat. No. 11,116,431, issued Sep. 14, 2021, 168 pages.
File History of U.S. Pat. No. 10,194,844, issued Feb. 5, 2019, 151 pages.
File History of U.S. Pat. No. 9,310,230, issued Apr. 12, 2016, 214 pages.
File History of U.S. Pat. No. 8,483,967, issued Jul. 9, 2013, 140 pages.
File History of U.S. Appl. No. 12/056,651, filed Mar. 27, 2008, 161 pages—Part 1.
File History of U.S. Appl. No. 12/056,651, filed Mar. 27, 2008, 162 pages—Part 2.
File History of U.S. Appl. No. 60/976,886, filed Oct. 2, 2007, 62 pages.
Mastrototaro, "The MiniMed Continuous Glucose Monitoring System," Diabetes Technology & Therapeutics, vol. 2, Suppl. 1, S-13-S-18 (2000) - 18 pages Appendix C.
Medtronic Receives FDA Approval for World's First Insulin Pump with Real-Time Continuous Glucose Monitoring, MiniMed Paradigm® REAL-Time System Allows Patients to Make Immediate Diabetes Management Decisions; Marks Major Step Toward an Artificial Pancreas, The Wayback Machine, 2 pages, Apr. 13, 2006.
Medtronic, The MiniMed Paradigm® Real-Time Insulin Pump and Continuous Glucose Monitoring System, Sensor Features User Guide, https://web.archive.org/web/20071028164026/http://www.medtronicdiabetes.com/pdf/x22_sensor_features.pdf 77 pages (2007).
Pantelopoulos et al., "A Survey on Wearable Biosensor Systems for Health Monitoring," 30th Annual International IEEE Embs Conference Vancouver, British Columbia, Canada, Aug. 20-24, 2008, 4887-4890 - 7 pages Appendix G.
Premarket Approval (PMA), Paradigm Real Time System, Fda, P980032, 3 p. Apr. 7, 2006.
Shenoi, "Introduction to Digital Signal Processing and Filter Design," Wiley-Interscience, 48 pages (2006).
Smith, "The Scientist and Engineer's Guide to Digital Signal Processing," California Technical Publishing, 2nd Ed., 46 pages (1999).
Velho et al., "In vivo calibration of a subcutaneous glucose sensor for determination of subcutaneous glucose kinetics," Diabetes, American Diabetes Association, 1 (3), 227-233 (1988) hal-01179359—10 pages Appendix P.
Waybackmachine, Medtronic, User Guides, https://web.archive.org/web/20071023121553/http://www.medtronicdiabetes.com/products/insulinpumps/userguides.html, 3 pages (2007).
Waybackmachine, Medtronic, User Guides, https://web.archive.org/web/20071023121437/http://www.medtronicdiabetes.com/products/insulinpumps/userguides.html 9 pages (2007).
Waybackmachine, Medtronic, User Guides, https://web.archive.org/web/20071023121607/http://www.medtronicdiabetes.com/products/insulinpumps/userguides.html, 3 pages (2007).
Waybackmachine, Medtronic, User Guides, https://web.archive.org/web/20071009143917/http://www.medtronicdiabetes.com/products/insulinpumps/ 2 pages (2007).
Waybackmachine, Medtronic, User Guides, https://web.archive.org/web/20071009144413/http://www.medtronicdiabetes.com/index.html, 2 pages (2007).

MULTI-RATE ANALYTE SENSOR DATA COLLECTION WITH SAMPLE RATE CONFIGURABLE SIGNAL PROCESSING

RELATED APPLICATIONS

The present application is a continuation of U.S. patent application Ser. No. 15/292,107 filed Oct. 12, 2016, which is a continuation of U.S. patent application Ser. No. 14/210,330 filed Mar. 13, 2014, now U.S. Pat. No. 9,474,475, which claims priority under 35 U.S.C. § 119(e) to U.S. Provisional Application No. 61/800,878 filed Mar. 15, 2013, entitled "Multi-Rate Analyte Sensor Data Collection with Sample Rate Configurable Signal Processing," the disclosures of each of which are incorporated herein by reference for all purposes.

The present application is related to U.S. application Ser. No. 14/210,312 filed Mar. 13, 2014, entitled "Noise Rejection Methods and Apparatus For Sparsely Sampled Analyte Sensor Data," U.S. Ser. No. 14/210,303 filed Mar. 13, 2014, entitled "Analyte Sensor Data Parameterized Filtering Methods and Apparatus," U.S. application Ser. No. 13/984,815 filed on Nov. 25, 2013, entitled "Software Applications Residing on Handheld Analyte Determining Devices" and U.S. application Ser. No. 12/807,278 filed Aug. 31, 2010, entitled "Medical Devices and Methods," all of which are incorporated herein by reference for all purposes.

BACKGROUND

The detection of the concentration level of glucose or other analytes in certain individuals may be vitally important to their health. For example, the monitoring of glucose levels is particularly important to individuals with diabetes or pre-diabetes. People with diabetes may need to monitor their glucose levels to determine when medication (e.g., insulin) is needed to reduce their glucose levels or when additional glucose is needed.

Devices have been developed for automated in vivo monitoring of analyte time series characteristics, such as glucose levels, in bodily fluids such as in the blood stream or in interstitial fluid. Some of these analyte level measuring devices are configured so that at least a portion of a sensor of an on-body device is positioned below a skin surface of a user, e.g., in a blood vessel or in the subcutaneous tissue of a user. As used herein, the term analyte monitoring system is used to refer to any type of in vivo monitoring system that uses a sensor disposed with at least a subcutaneous portion to measure and store sensor data representative of analyte concentration levels automatically over time. Analyte monitoring systems include both (1) systems such as continuous glucose monitors (CGMs) which transmit sensor data continuously or at regular time intervals (e.g., once per minute) to a processor/display unit and (2) systems that transfer stored sensor data in one or more batches in response to a scan request from a processor/display unit (e.g., based on an activation action and/or proximity using, for example, a near field communications protocol).

Monitoring a user's analyte level that has a relatively high rate of change can require collecting and storing a relatively large amount of sensor data. However, in an effort to minimize the cost, size, and power requirements of analyte monitoring systems, it is desirable to minimize the amount of memory required for use within the on-body device. Thus, what is needed are systems, methods and apparatus that can provide a sufficient amount of sensor data to accurately determine a user's analyte level but at the same time minimize the memory requirements.

SUMMARY

The present disclosure provides systems, methods, and apparatus for determining an estimate of an analyte level over time. The invention includes sampling sensor data using an analyte sensor positioned at least partially subcutaneously, storing a first dataset of sensor data at a first rate, storing a second dataset of sensor data at a second rate, determining an estimated analyte level based on the first and second datasets, and outputting the estimated analyte level to a display. Storing the first and second datasets can include storing the first and second datasets concurrently and the first rate can be higher than the second rate. Storing the first dataset can also include storing the first dataset in a first memory buffer and storing the second dataset can include storing the second dataset in a second memory buffer. The first memory buffer can have a size that is different than a size of the second memory buffer. Storing the first and second datasets can include storing the first and second datasets in separate memory buffers within sensor electronics disposed with an on body device. The present disclosure further includes transferring the first and second datasets from the memory buffers to a receiver for signal processing. Storing the first and second datasets can include storing the first and second datasets in separate memory partitions of a single memory device. Determining an estimated analyte level can include determining a discrete time approximation of a filter model represented by a state space realization.

The invention also includes a computer system and a computer program product for filtering analyte monitoring system sensor data. Numerous other aspects and embodiments are provided. Other features and aspects of the present disclosure will become more fully apparent from the following detailed description, the appended claims, and the accompanying drawings.

BRIEF DESCRIPTION OF THE DRAWINGS

The accompanying drawings, which are incorporated herein, form part of the specification. Together with this written description, the drawings further serve to explain the principles of, and to enable a person skilled in the relevant arts, to make and use the present disclosure.

DETAILED DESCRIPTION

Figure 1:
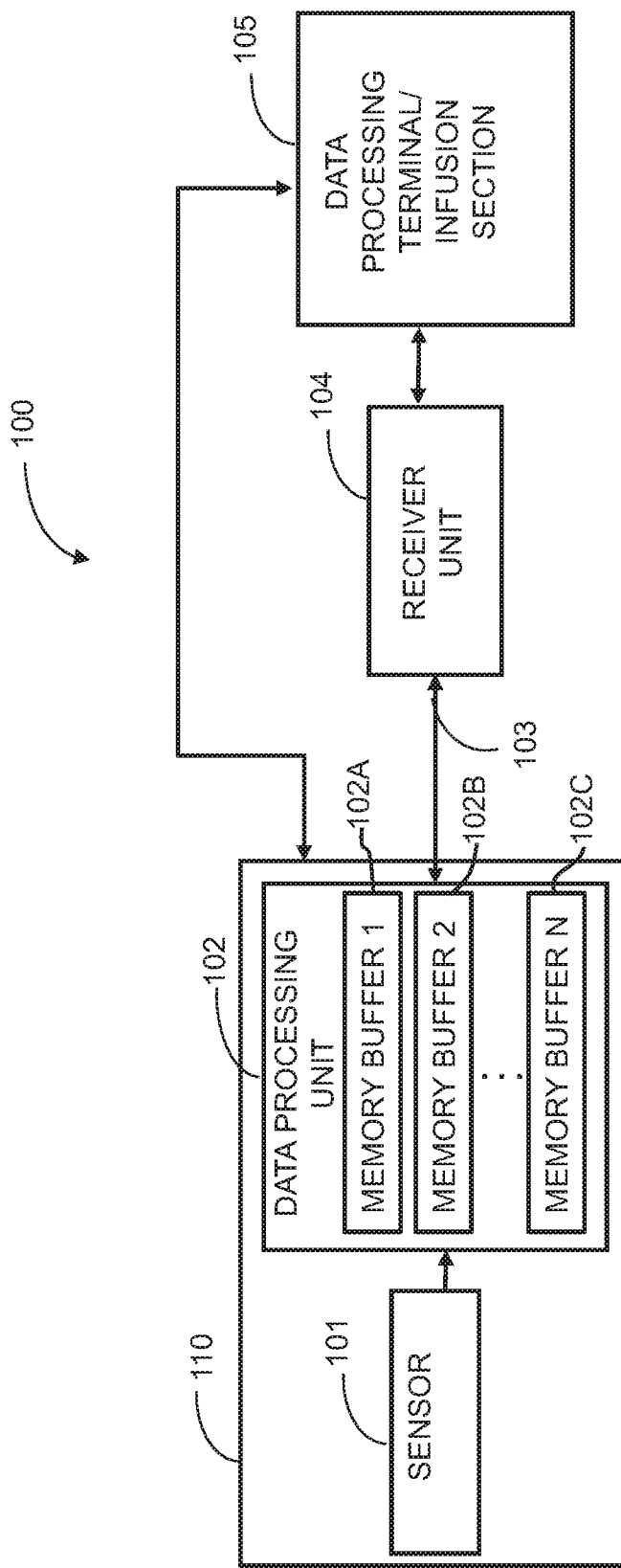
FIG. 1 depicts a data monitoring and management system such as, for example, an analyte (e.g., glucose) monitoring system in accordance with some embodiments of the present disclosure.

Before the embodiments of the present disclosure are described, it is to be understood that this invention is not limited to the particular embodiments described, as such may, of course, vary. It is also to be understood that the terminology used herein is for the purpose of describing particular embodiments only, and is not intended to be limiting, since the scope of the embodiments of the invention will be limited only by the appended claims.

The present disclosure provides systems, methods, and apparatus to monitor an analyte level using a minimized amount of memory and both a maximized time window of available past sensor data and a maximized density of recent sensor data. At the same time, the present disclosure facilitates artifact rejection and lag correction. The invention uses a combination of a hardware configuration (e.g., memory arrangement) and a signal processing method to achieve these features and benefits.

The invention can be applied to sensor data from an analyte monitoring system, such as, for example, any type of in vivo monitoring system that uses a sensor disposed with at least a subcutaneous portion to measure and store sensor data representative of analyte concentration levels automatically over time. Analyte monitoring systems can include CGMs which are programmed to transmit sensor data according to a predetermined transmission schedule, continuously, or at regular time intervals to a processor/display unit and systems that transfer stored sensor data in one or more batches in response to a request from a processor/display unit, i.e., not according to a predetermined transmission schedule.

According to some embodiments of the present disclosure, datasets related to a patient's monitored analyte concentration level (herein referred to as "sensor data") over time are received from an on-body device that includes an analyte sensor. The sensor data can include datasets with differing data rates. In some embodiments, the sensor data can represent a collection of data that is transmitted from an on-body device at several different times during a wear period of the on-body device. In some other embodiments, the sensor data can represent data collected and stored over an entire wear period of an on-body device and only transmitted from the on-body device at the end of the wear period or at the end of the useful life of the on-body device. In other words, the sensor data can be transmitted continuously, on a regular schedule, in multiple batches over time, in batches on demand, or in a single batch.

The embodiments of the present disclosure can also be applied to any analyte concentration level determination system that may exhibit or at least be suspected of exhibiting, or that may be susceptible to noise or artifacts in the sensor data. Embodiments of the invention are described primarily with respect to continuous glucose monitoring devices and systems but the present disclosure can be applied to other analytes and analyte characteristics, as well as data from measurement systems that transmit sensor data from a sensor unit to another unit such as a processing or display unit in response to a request from the other unit. For example, other analytes that can be monitored include, but are not limited to, acetyl choline, amylase, bilirubin, cholesterol, chorionic gonadotropin, creatine kinase (e.g., CK-MB), creatine, DNA, fructosamine, glutamine, growth hormones, hormones, ketones, lactate, peroxide, prostate-specific antigen, prothrombin, RNA, thyroid stimulating hormone, and troponin. The concentration of drugs, such as, for example, antibiotics (e.g., gentamicin, vancomycin, and the like), digitoxin, digoxin, drugs of abuse, theophylline, and warfarin, can also be monitored. In the embodiments that monitor more than one analyte, the analytes can be monitored at the same or different times. The present disclosure also provides numerous additional embodiments.

Embodiments of the present disclosure may include a programmed computer system adapted to receive and store data from an analyte monitoring system. The computer system can include one or more processors for executing instructions or programs that implement the methods described herein. The computer system can include memory and persistent storage devices to store and manipulate the instructions and sensor data received from the analyte monitoring system. The computer system can also include communications facilities (e.g., wireless and/or wired) to enable transfer of the sensor data from the analyte monitoring system to the computer. The computer system can include a display and/or output devices for presenting the sensor data to a user. The computer system can include input devices and various other components (e.g., power supply, operating system, clock, etc.) that are typically found in a conventional computer system. In some embodiments, the computer system can be integral to the analyte monitoring system. For example, the computer system can be embodied as a handheld or portable receiver unit within the analyte monitoring system or, in some embodiments, as a processor or logic circuit within the sensor electronics of an on-body device of the analyte monitoring system.

The various methods described herein for performing one or more processes also described herein can be embodied as computer programs (e.g., computer executable instructions and data structures) developed using an object oriented programming language that allows the modeling of complex systems with modular objects to create abstractions that are representative of real world, physical objects and their interrelationships. However, any practicable programming language and/or techniques can be used. The software for performing the inventive processes, which can be stored in a memory or storage device of the computer system described herein, can be developed by a person of ordinary skill in the art based upon the present disclosure and can include one or more computer program products. The computer program products can be stored on a computer readable medium such as a server memory, a computer network, the Internet, and/or a computer storage device. Note that in some cases the methods embodied as software may be described herein with respect to a particular order of operation or execution. However, it will be understood by one of ordinary skill that any practicable order of operation or execution is possible and such variations are contemplated by this specification of the present disclosure.

Filtering noise, compensating for undesired dynamics, and responding to variable availability of data points can be significant in generating an accurate representation of an analyte concentration level using an analyte monitoring system. In some analyte monitoring systems, for example, the sensor data can include a window of sampled data long enough to cover a significant portion of a day, e.g., a 6 to 24 hour window with data points collected every 10 to 20 minutes. However, significant changes in the measurement of an analyte level can occur in less than 10 minutes which such systems may not be able to detect. In addition to filtering noise and artifacts, some of the data points may not be available due to data quality issues. A reliable analyte measurement system according to the present disclosure can filter noise, correct for artifacts, compensate for undesired dynamics, and recover missing data using the remaining data.

In an analyte measurement system adapted to determine and represent a user's glucose concentration level, for example, a filter is used to process sensor data received as signals by the sensor electronics within the on-body device. A component of the filter utilizes several pre-conditioned sensor signals, z, at various time instances, to generate an output that represents the best estimate of reference glucose and reference glucose rate of change values.

FIG. 1 depicts an illustrative embodiment of a data monitoring and management system such as, for example, an analyte (e.g., glucose) monitoring system in accordance with the present disclosure. Note that the present disclosure is frequently described herein with reference to diabetes treatment based on measurement and control of glucose levels using insulin, however, the present disclosure is applicable to treatment of many different diseases based on measurement and/or control of many different analytes using many different medications. As shown in FIG. 1, an analyte monitoring system 100 can include a sensor 101, a data processing unit (e.g., sensor electronics) 102 connectable to the sensor 101, and a receiver unit 104 which is configured to communicate with the data processing unit 102 via a communication link 103. In some embodiments of the present disclosure, the sensor 101 and the data processing unit (e.g., sensor electronics) 102 can be configured as a single integrated assembly 110. In some embodiments, the integrated sensor and sensor electronics assembly 110 can be configured as an on-body device wearable by a user. In such embodiments, the on-body device can be configured, for example, for wireless radio frequency identification (RFID) and/or radio frequency (RF) communication with a reader device/receiver unit 104, and/or an insulin pump.

In some embodiments, the receiver unit 104 can be further configured to transmit data to a data processing terminal 105 to evaluate or otherwise process or format data received by the receiver unit 104. The data processing terminal 105 can be configured to receive data directly from the data processing unit 102 via a communication link which can optionally be configured for bi-directional communication. Further, the data processing unit 102 can include a transmitter or a transceiver to transmit and/or receive data to and/or from the receiver unit 104, the data processing terminal 105.

Only one sensor 101, data processing unit 102, and data processing terminal 105 are shown in the embodiment of the analyte monitoring system 100 illustrated in FIG. 1. However, it will be appreciated by one of ordinary skill in the art that the analyte monitoring system 100 can include more than one sensor 101 and/or more than one data processing unit 102, and/or more than one data processing terminal 105.

The analyte monitoring system 100 can be a continuous monitoring system, or semi-continuous, or a discrete monitoring system. In a multi-component environment, each component can be configured to be uniquely identified by one or more of the other components in the system so that communication conflict can be readily resolved between the various components within the analyte monitoring system 100. For example, unique IDs, communication channels, and the like, can be used.

In certain embodiments, the sensor 101 is physically positioned in or on the body of a user whose analyte level is being monitored. The data processing unit 102 is coupleable to the sensor 101 so that both devices are positioned in or on the user's body, with at least a portion of the analyte sensor 101 positioned transcutaneously. The data processing unit 102 in certain embodiments can include a portion of the sensor 101 (proximal section of the sensor in electrical communication with the data processing unit 102) which is encapsulated within or on a printed circuit board of the data processing unit 102 with, for example, potting material or other protective material. The data processing unit 102 performs data processing functions, where such functions can include but are not limited to, storing, filtering and encoding of data signals, each of which corresponds to a sampled analyte level of the user, for transmission to the receiver unit 104 via the communication link 103. In some embodiments, the sensor 101 or the data processing unit 102 or a combined sensor/data processing unit can be wholly implantable under the skin layer of the user.

In some embodiments, the receiver unit 104 can include an analog interface section including an RF receiver and an antenna that is configured to communicate with the data processing unit 102 via the communication link 103, and a data processing section for processing the received data from the data processing unit 102 such as data decoding, error detection and correction, data clock generation, and/or data bit recovery.

Referring still to FIG. 1, the data processing terminal 105 can include an infusion device such as an insulin infusion pump or the like, which can be configured to administer insulin to patients, and which can be configured to communicate with the receiver unit 104 for receiving, among others, the measured analyte level. Alternatively, the receiver unit 104 can be configured to integrate an infusion device therein so that the receiver unit 104 is configured to administer insulin (or other appropriate drug) therapy to patients, for example, for administering and modifying basal profiles, as well as for determining appropriate boluses for administration based on, among others, the detected analyte levels received from the data processing unit 102. An infusion device can be an external device or an internal device (wholly implantable in a user). An insulin bolus calculator can be operatively coupled to the receiver unit 104 to determine an insulin dose that is required based upon the analyte data received from the sensor device/electronics.

In some embodiments, the data processing terminal 105, which can include an insulin pump, can be configured to receive the analyte signals from the data processing unit 102, and thus, incorporate the functions of the receiver unit 104 including data processing for managing the patient's insulin therapy and analyte monitoring.

In some embodiments, the data processing unit 102 (e.g., the sensor electronics) can include one or more memory buffers 102A, 102B, 102C used by the data processing unit 102 to store sensor data from the sensor 101. The memory buffers 102A, 102B, 102C can be embodied as first-in-first-out (FIFO) buffers that can hold one or more sets of recent sensor data so that the sensor data can be transferred to the receiver unit 104. The sets of sensor data can each represent a moving time window of data points collected or sampled by the sensor. As time passes, new data is stored in the memory buffers 102A, 102B, 102C and older data is overwritten such that at any given time, a memory buffer 102A, 102B, 102C holds a collection of the most recent data points received and extending back in time based on the size of the buffer and the storage rate.

The storage rate at which the sensor data is written into the memory buffers 102A, 102B, 102C can correspond to the sampling rate of the sensor or a selected lower rate. The size of the time window of data points can correspond to the size of the associated memory buffer 102A, 102B, 102C selected to store the data at the storage rate. In some embodiments, different memory buffers 102A, 102B, 102C can be different sizes and can store sensor data at different rates. In other words, the density of the data (e.g., the number of data points stored in a given amount of time) in a particular memory buffer can be different for different memory buffers 102A, 102B, 102C.

In some embodiments, the sampling rate of the sensor is constant and the storage rates in the memory buffers are based on a selected fraction of the sampling rate. For example, where the sensor sampling rate is once every minute; the storage rate in a first memory buffer 102A can also be once every minute while the storage rate in a second memory buffer 102B can be once every twenty minutes. If both buffers 102A, 102B each include, for example, 0.5 Kb (i.e., 512) of storage addresses, the first memory buffer 102A can hold an approximately 8.5 hour time window of data points while the second memory buffer 102B can hold an approximately seven day time window of data points. In some embodiments, the sampling rate may be once every two minutes, or once every five minutes, or other suitable sampling rate, and in which case, the storage rate in the first memory buffer 102 and the storage rate in the second memory buffer 102B may correspondingly change to different suitable rates.

In some embodiments, the storage rate can be varied. For example, the rate at which the data processing unit 102 stores data into one or more of the memory buffers 102A, 102B, 102C can be set based upon a selected variable. In some embodiments, based upon the rate of change of values of the sensor data, it may be desirable to store more or less data per unit time. For example, where the value of the sensor data is relatively constant, the sensor data may only be stored infrequently and where the sensor data is changing rapidly, the sensor data may be stored relatively frequently. In such embodiments, information that can be used to determine the storage rate (e.g., timestamp, time between data points, etc.) can also be stored. This allows the amount of memory to be minimized while still providing increased sensor data density when significant events may be occurring.

In some embodiments, the memory buffers 102A, 102B, 102C can be implemented as different memory devices (e.g., different memory integrated circuits) or as a singled memory device partitioned into different sections. Any practicable type of memory can be used to implement the memory buffers 102A, 102B, 102C.

Figure 2:
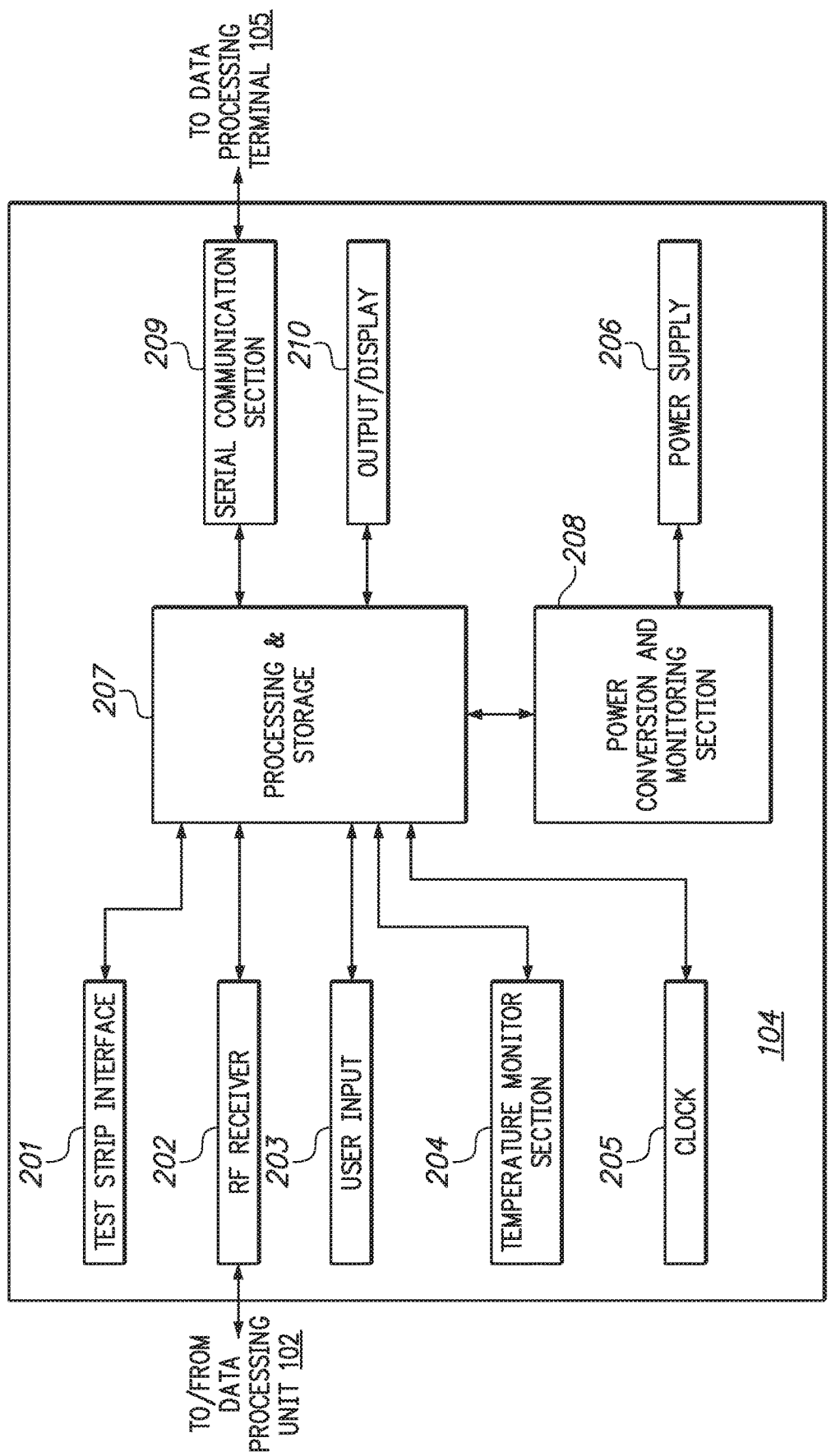
FIG. 2 is a block diagram of a receiver/monitor unit such as that shown in FIG. 1 in accordance with some embodiments of the present disclosure.

FIG. 2 is a block diagram of a receiver/monitor unit 104 or insulin pump such as that shown in FIG. 1 in accordance with certain embodiments. The receiver unit 104 can include one or more of: a blood glucose test strip interface 201, an RF receiver 202, an input 203, a temperature detection section 204, and a clock 205, each of which is operatively coupled to a processing and storage section 207. In certain embodiments, a receiver, such as receiver unit 104, also includes a power supply 206 operatively coupled to a power conversion and monitoring section 208. Further, the power conversion and monitoring section 208 is also coupled to the receiver's processor 207. Moreover, also shown are a receiver serial communication section 209, and an output 210, each operatively coupled to the processing and storage unit 207. The receiver unit 104 can include user input and/or interface components or can be free of user input and/or interface components.

In some embodiments, the RF receiver 202 is configured to communicate, via the communication link 103 (FIG. 1) with the data processing unit (e.g., sensor electronics) 102, to receive encoded data from the data processing unit 102 for, among others, signal mixing, demodulation, and other data processing. The input 203 of the receiver unit 104 is configured to allow the user to enter information into the receiver unit 104 as needed. In one aspect, the input 203 can include keys of a keypad, a touch-sensitive screen, and/or a voice-activated input command unit, and the like. The temperature monitor section 204 can be configured to provide temperature information of the receiver unit 104 to the processing and control section 207, while the clock 205 provides, among others, real time or clock information to the processing and storage section 207.

Each of the various components of the receiver unit 104 shown in FIG. 2 is powered by the power supply 206 (or other power supply) which, in some embodiments, includes a battery. The output/display 210 of the receiver unit 104 is configured to provide, among others, a graphical user interface (GUI), and can include a liquid crystal display (LCD) for displaying information and/or allowing a user to enter information. The receiver unit 104 can also include a storage section such as a programmable, non-volatile memory device as part of the processor 207, or provided separately in the receiver unit 104, operatively coupled to the processor 207.

Conventional analyte monitors typically use a single memory buffer to store sensor data at a single rate. To be able to accurately represent an analyte level over time however, including correcting for lag, filtering noise and artifacts, and correcting for missing or unavailable data points, such a system would need to store data at a relatively fast rate (e.g., once per minute). Further, in order to attain a longer historical duration of analyte values, a conventional on body unit would need to be able to store a relatively large amount of data. Together, these requirements result in an on body device that includes an undesirably large memory capacity. For example, if the required data density requires a sample rate of once per three minutes, and twenty-four hours of duration needs to be covered, then the memory buffer must store 1+(24*(60/3))=481 data points. Then, conventional signal processing method that assumes a constant sample rate can be used.

Figure 3:
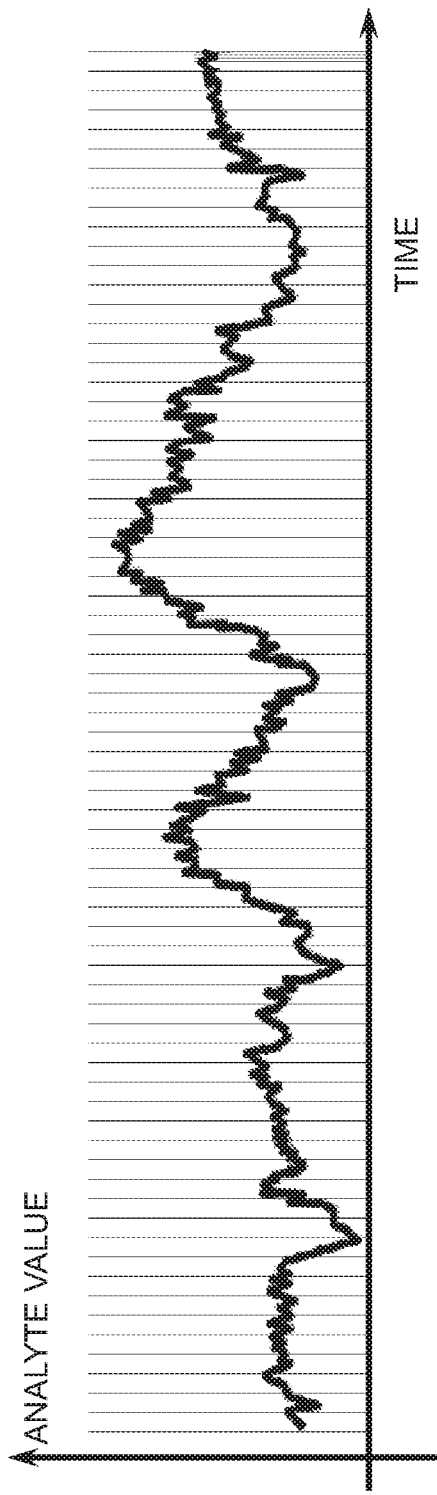
FIG. 3 depicts an example graph illustrating a plot of analyte level over time in accordance with some embodiments of the present disclosure.

The present disclosure overcomes these requirements by providing two or more memory buffers within the on body device that are configured to store sensor data at two different rates, coupled with a signal processing method that can operate on more than one sample rate setting. In some embodiments, one relatively slow data rate over a relatively long duration is taken to maximize coverage of past data, and one relatively fast data rate over a relatively short duration is taken to maximize density of recent data. One memory buffer stores data collected at the slow rate, and another memory buffer stores data collected at the fast sample rate. For example, as illustrated in FIG. 3, consider a first memory buffer that stores sensor data at a relatively slow rate (e.g., once per 20 minutes) over a relatively long period (e.g., 24 hours) so that a large time window of data points (e.g., 72 data points) is available using a relatively small memory. A second memory buffer stores data at a relatively fast rate (e.g., once per three minutes) over a relatively short period (e.g., 9 minutes) so that detailed sensor data is available but also using only a relatively small memory (e.g., 4 data points). This arrangement allows for both long coverage of historical analyte data and high density data that is useful to generate accurate real-time analyte level output without requiring a large memory capacity within the on-body device. Compared with the conventional single rate method which would store 481 data points, the present disclosure can estimate the analyte just as accurately with only storing 1+(24*(60/20))+1+(9/3)=77 data points, i.e., an approximately 84% reduction in this example.

The present disclosure also includes providing methods of combining sensor data of different rates so that the analyte monitoring system can accurately filter the sensor data and correct for lag. For example, the calculated analyte value y is a function of the preconditioned sensor data z and calculated rates of change at different sample rates;

$$y(k)=z(k)+a1v1+a2v2+\ldots+aNvN,$$

with each v1 through vN calculated by $$[z(k)-z(k-T1)]/T1,[z(k)-z(k-T2)]/T2,\ldots,[z(k)-z(k-TN)]/TN$$

Figure 4:
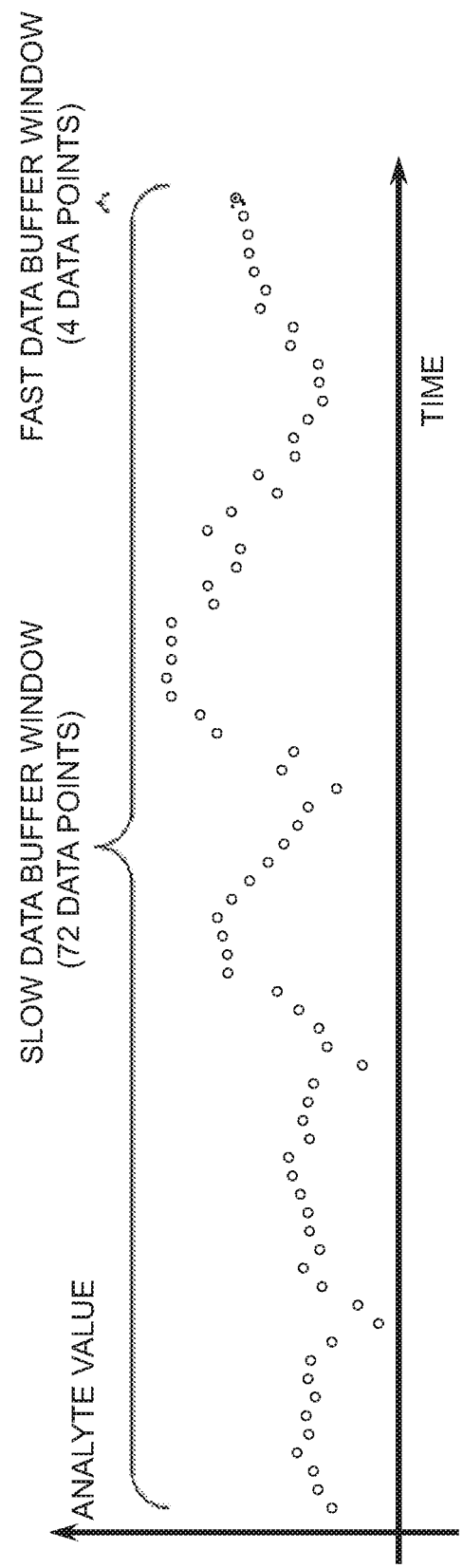
FIG. 4 depicts an example graph illustrating a plot of sensor data points collected over time in accordance with some embodiments of the present disclosure.
Figure 5:
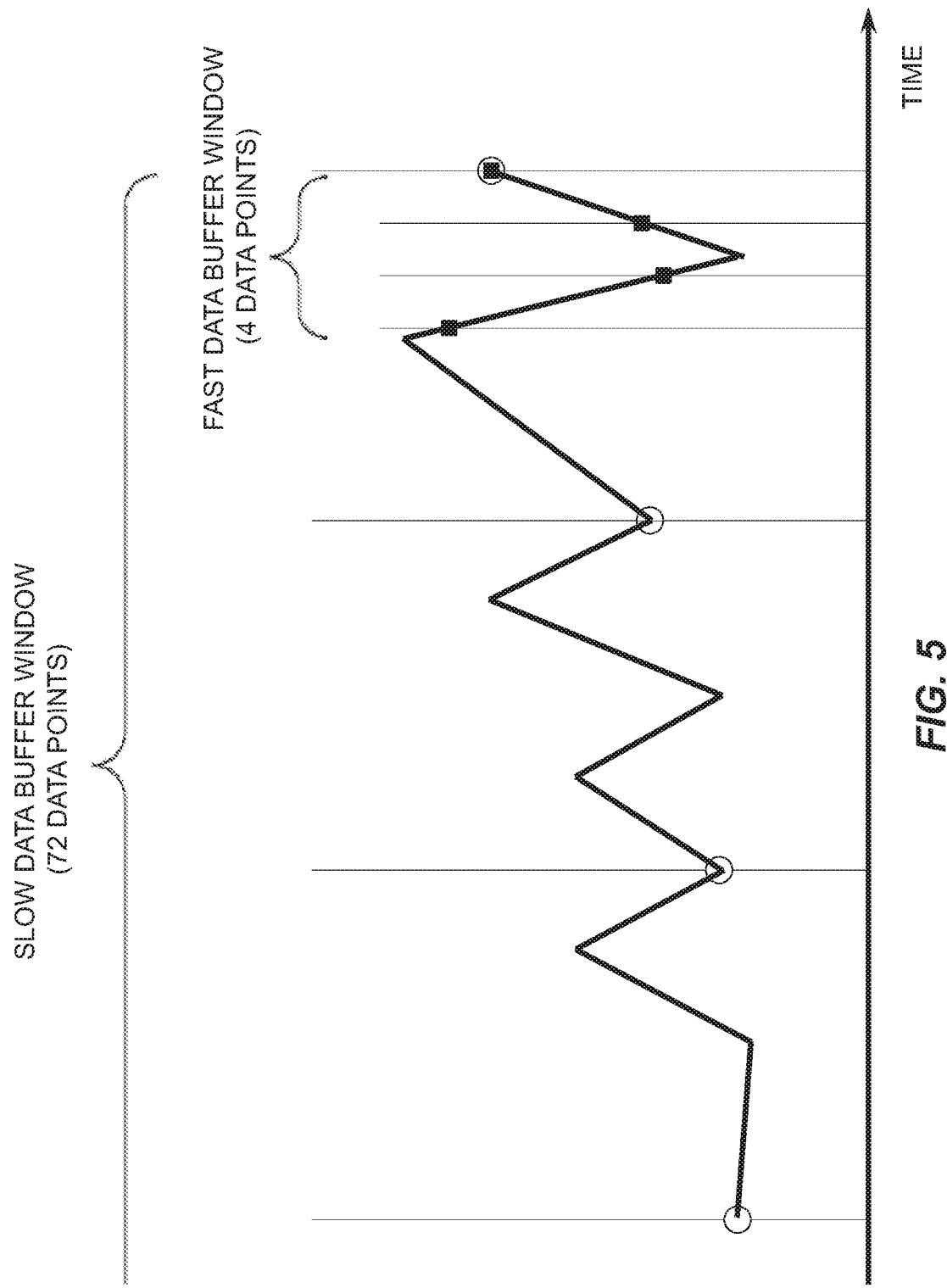
FIG. 5 depicts an example graph illustrating a magnified view of the analyte level plot of FIG. 3 overlaid on the sensor data point plot of FIG. 4 in accordance with some embodiments of the present disclosure.

For any time instance where an output value is to be determined, a combination of nearby sensor data and a dynamic model describing the system is used to calculate the output. FIG. 4 and the magnified view provided in FIG. 5 illustrate the use of input data stored in the manner described, converted into output values at various instances.

In another example, if the latest 30 minutes are to be covered with relatively high data density, then a sample rate of once per 3 minutes will mean the first memory buffer, Fast Data buffer, to store 1+(30/3)=11 data points. For 10 hours of past data coverage with a rate of once per 20 minutes, the second memory buffer, Slow Data buffer, will store 1+(10*(60/20))=31 data points. Then, the total memory buffer size is for storing 42 data points. This is significantly less than the conventional method.

In another example, if the latest 15 minutes are to be covered with an even higher data density relative to the example above, then a sample rate of once every minute will mean the Fast Data buffer will store 1+(15/1)=16 data points. For 8 hours of past data coverage with a rate of once per 15 minutes, the Slow Data memory buffer will store 1+(8*(60/15))=33 data points. Analyte values near the sensor measured in vivo are stored into the two memory storage buffers as input data for the signal processing method. If memory storage with increments in bytes is used, reserving 2 bytes for Fast Data and 4 bytes for Slow Data yields 16 and 32 data points, respectively.

In another embodiment, a single memory buffer can store data and a time index (e.g., a timestamp, a delta time between data points, etc.), wherein the time interval from one sample to the next is determined to optimize data storage efficiency. Previously incorporated US Provisional Application Ser. No. 61/485,840 describes details of how such an arrangement can be implemented.

In some embodiments, the basic calculation can be derived a priori based on a dynamic model in the continuous time domain. For example, let the output y at time t, y(t), be a function of a set of internal states x(t) and a set of sensor data u(t), described in terms of state space as:

$$y(t)=Cx(t)$$

$$dx(t)/dt=Ax(t)+Bu(t)$$

Assuming time invariant parameter matrices A, B, and C, design of the filter in terms of noise rejection and dynamic compensation such as lag correction can be achieved using loop shaping theory or other methods, noting that the Laplace transform of the state space model above is:

$$Y(s)=C[sI-A]^{-1}BU(s)$$

Then, for the case where two memory buffers with different sample times store sensor data, the output y at discrete time instance k can be calculated by using a discrete time approximation of an infinite impulse response (IIR) filter model represented by the state space realization above. The sample time is a function of the time interval between nearest sensor data points eligible for the output at time k.

In another example and without loss of generality, suppose x(t) and u(t) are both single dimensional time series, so that A, B, and C are scalars. Let A=−0.1, B=0.1, C=1, values which are determined a priori during the system development. One discrete time realization of this system, using zero order hold, for any discrete time instance k is then $$y(k)=Ady(k-1)+Bdu(k-1),$$

where:

$$Ad=e^{A*Ts}$$

and $$Bd=[Ad--1]*B/A.$$

Note that the discrete time parameters Ad and Bd are now dependent on the sample time Ts (=time spacing between adjacent data points). The output calculation y now depends on a model whose parameters can vary from one instance to another. If the nearby data points are all from Fast Data collected, e.g., once per minute, but the nearest available raw data is 3 minutes away, letting Ts=3 minutes, Ad=1.35, Bd=−0.35. If the nearby data points are one from Fast Data, and another from Slow Data, and the time interval happens to be 8 minutes, Ad=2.23, Bd=−1.23. Note that for models requiring more than two input data points, the state space parameters do not remain scalars.

While the previous example utilizes a state space model framework, other digital filter structures (e.g., described in terms of a Finite Impulse Response (FIR) filter) can be used. Unlike the state space derived filter, synthesis of FIR parameters given varying sample times is more complex. An example method for synthesizing parameters using the FIR approach is described in previously incorporated U.S. application Ser. No. 14/210,303 entitled "Analyte Sensor Data Parameterized Filtering Methods and Apparatus."

In some embodiments, when a single memory buffer with irregular sample time is used, a method based on regularization can be used to calculate the output. Examples of the method of regularization are described in *Numerical Recipes in C: The Art of Scientific Computing*, 2 ed., Cambridge University Press, 2002, by W. H. Press, et al. and in "Nonparametric input estimation in physiological systems: Problems, methods, and case studies," *Automatica*, vol. 33, pp. 851-870, 1997, by G. DeNicolao, et al., which are hereby incorporated herein by reference for all purposes. Regularization allows for each of the source data to be assigned different levels of confidence, wherein the smoothed output at any time instance is more likely to match the source data at that time instance when the source data point has a larger confidence (or equivalently, a smaller assumed measurement error model) relative to other neighboring source data points.

For robustness against artifacts, more than one estimate of the output at any instance k can be calculated using different combinations of sensor data. Alternatively, the dynamic model assumes a processed sensor data as its input stream, with this input stream made available at a desired interval, and the processed sensor data at those desired intervals are generated from sensor data with different storage rate intervals. An example method for generating processed sensor data is described in previously incorporated U.S. application Ser. No. 14/210,312 entitled "Noise Rejection Methods and Apparatus For Sparsely Sampled Analyte Sensor Data."

Figure 6:
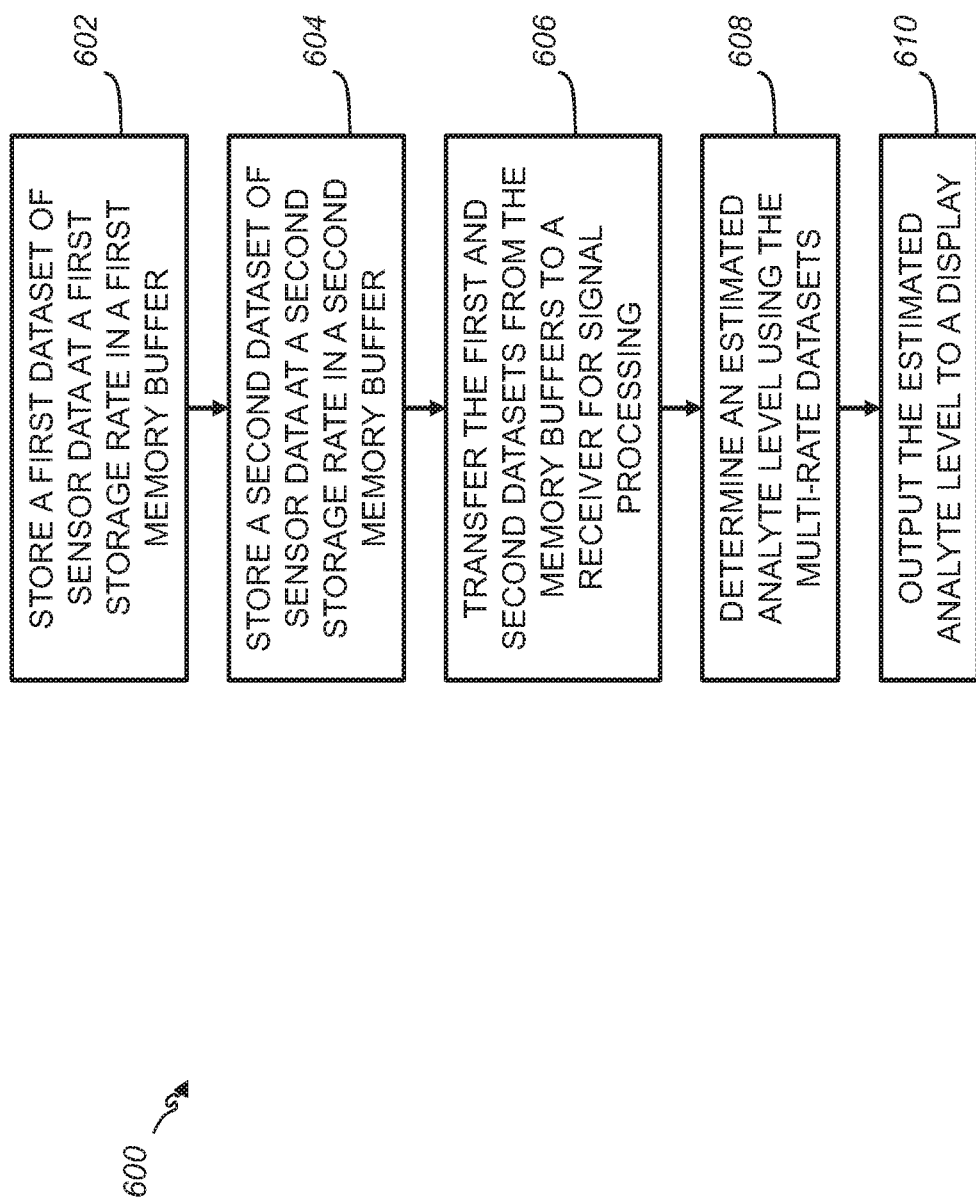
FIG. 6 is a flow chart depicting an example method in accordance with some embodiments of the present disclosure.

Turning now to FIG. 6, a flow chart 600 depicting example methods of the present disclosure is provided. As indicated above, the methods of the present disclosure can be implemented on a computer or other processing device. Also, the particular order in which the steps of the invention are presented here does not represent the only order in which the steps can be performed.

In some embodiments, a first dataset of sensor data is stored at a first storage rate in a first memory buffer (602) and a second dataset of sensor data is stored at a second storage rate in a second memory buffer (604). The datasets can be stored concurrently. The storage rates are different and the memory buffers are also different. For example, the first rate can be a relatively fast rate while the second rate can be a relatively slow rate. The first memory buffer can be smaller than the second memory buffer. Sensor data is stored in the memory buffers over different periods of time. For example, the sensor data stored in the first memory buffer at the relatively fast rate can be stored over a relatively short time period after which the first buffer begins to get overwritten. Meanwhile the sensor data stored in the second memory buffer at the relatively slow rate can be stored over a relatively long time period after which the second buffer begins to get overwritten. The first and second datasets are transferred from the memory buffers to a receiver for signal processing (606).

Using the multi-rate datasets, an estimated analyte level is next determined (608). A composite dataset can be generated based on a selection of data points from the first and second datasets. Filter parameters are then determined using the storage rates of the selected data points in the composite dataset. In some embodiments, a predetermined dynamic filter model in the continuous time domain is used. For example, let the output y at time t, y(t), be a function of a set of internal states x(t) and a set of sensor data u(t), described in terms of state space as:

$$y(t)=Cx(t)$$

$$dx(t)/dt=Ax(t)+Bu(t).$$

Then the output y at discrete time instance k can be calculated by using a discrete time approximation of the filter model represented by the above state space realization. The storage time is a function of the time interval between the nearest sensor data points eligible for the output at time k. More generally, an estimated analyte level is determined based on one or more filters using the set of filter parameters and the composite dataset. The estimated analyte level is then output to a display (610).

In the manner described above, in certain embodiments of the present disclosure, there is provided a method comprising: sampling sensor data using an analyte sensor, storing a first dataset of the sensor data at a first rate, storing a second dataset of the sensor data at a second rate, determining an estimated analyte level based on the first and second datasets of the sensor data, and outputting the estimated analyte level to a display.

In certain embodiments, storing the first and second datasets of the sensor data includes storing the first and second datasets of the sensor data concurrently, and the first rate is higher than the second rate.

In certain embodiments, storing the first dataset of the sensor data includes storing the first dataset of the sensor data in a first memory buffer, storing the second dataset of the sensor data includes storing the second dataset of the sensor data in a second memory buffer, and the first memory buffer has a size that is different than a size of the second memory buffer.

In certain embodiments, storing the first and second datasets of the sensor data includes storing the first and second datasets of the sensor data in separate memory buffers within sensor electronics disposed with an on body device.

In certain embodiments, the method further comprises transferring the first and second datasets of the sensor data from the separate memory buffers to a receiver for processing.

In certain embodiments, storing the first and second datasets of the sensor data includes storing the first and second datasets of the sensor data in separate memory partitions of a single memory device.

In certain embodiments, determining the estimated analyte level includes determining a discrete time approximation of a filter model represented by a state space realization.

In certain embodiments, determining the estimated analyte level includes: generating a composite dataset based on a selection of all or a subset of data points from the first and second datasets of the sensor data; determining a set of filter parameters based on rates of the composite dataset, and determining the estimated analyte level based on one or more filters using the set of filter parameters and the composite dataset.

A method in certain embodiments comprises sampling sensor data using an analyte sensor, storing a plurality of datasets of the sensor data, each at a different rate, determining an estimated analyte level based on the plurality of datasets of the sensor data, and outputting the estimated analyte level to a display.

In certain embodiments, storing the plurality of datasets of the sensor data includes storing the plurality of datasets of the sensor data, each in a different memory buffer.

In certain embodiments, storing the plurality of datasets of the sensor data includes storing each dataset in separate memory buffers within sensor electronics disposed with an on body device.

In certain embodiments, the method further comprises transferring the plurality of datasets of the sensor data from the separate memory buffers to a receiver for signal processing.

In certain embodiments, storing the plurality of datasets of the sensor data includes storing the plurality of datasets of the sensor data in separate memory partitions of a single memory device.

In certain embodiments, determining the estimated analyte level includes determining a discrete time approximation of a filter model represented by a state space realization.

In certain embodiments, determining the estimated analyte level includes: generating a composite dataset based on a selection of all or a subset of data points from the plurality of datasets of sensor data, determining a set of filter parameters based on rates of the composite dataset, and determining the estimated analyte level based on one or more filters using the set of filter parameters and the composite dataset.

A system for determining an estimate of an analyte level over time in certain embodiments comprises a processor, and a memory coupled to the processor, the memory storing processor executable instructions to: sample sensor data using an analyte sensor, store a plurality of datasets of the sensor data, each at a different rate, determine an estimated analyte level based on the plurality of datasets of the sensor data, and output the estimated analyte level to a display.

In certain embodiments, the memory including processor executable instructions to store the plurality of datasets of the sensor data includes an instruction to store each dataset in a different memory buffer.

In certain embodiments, the memory including processor executable instructions to store the plurality of datasets of the sensor data includes an instruction to store each dataset in separate memory buffers within sensor electronics disposed with an on body device.

In certain embodiments, the memory including processor executable instructions further includes an instruction to transfer the plurality of datasets of the sensor data from the separate memory buffers to a receiver for signal processing.

In certain embodiments, the memory including processor executable instructions to store the plurality of datasets of the sensor data includes an instruction to store the plurality of datasets of the sensor data in separate memory partitions of a single memory device.

In certain embodiments, the memory including processor executable instructions to determine the estimated analyte level includes an instruction to determine a discrete time approximation of a filter model represented by a state space realization.

In certain embodiments, the memory including processor executable instructions to determine the estimated analyte level includes instructions to: generate a composite dataset based on a selection of all or a subset of data points from the plurality of datasets of sensor data, determine a set of filter parameters based on rates of the composite dataset, and determine the estimated analyte level based on one or more filters using the set of filter parameters and the composite dataset.

An on body device for an analyte monitoring system in certain embodiment includes an analyte sensor configured to be positioned at least partially subcutaneously, sensor electronics coupleable to the analyte sensor, wherein the sensor electronics includes a first memory buffer configured to store sensor data at a first data rate, and a second memory buffer configured to store sensor data at a second data rate.

Various other modifications and alterations in the structure and method of operation of the embodiments of the present disclosure will be apparent to those skilled in the art without departing from the scope and spirit of the present disclosure. Although the present disclosure has been described in connection with certain embodiments, it should be understood that the present disclosure as claimed should not be unduly limited to such embodiments. It is intended that the following claims define the scope of the present disclosure and that structures and methods within the scope of these claims and their equivalents be covered thereby.

What is claimed is:

1. An apparatus comprising:
   one or more processors configured to receive sensor data from an analyte sensor; and
   a memory storing instructions which, when executed by the one or more processors, causes the one or more processors to:
   generate a composite dataset that comprises at least a first dataset and a second dataset based on the sensor data received from the analyte sensor, wherein the first dataset has a first data rate and the second dataset has a second data rate, and wherein each of the first data rate and the second data rate is based on a different factor of a sampling rate of the analyte sensor; and
   estimate an analyte level based on the first dataset and the second dataset included in the composite dataset.

2. The apparatus of claim 1, wherein the first data rate is greater than the second data rate.

3. The apparatus of claim 1, wherein the composite dataset comprises more of the second dataset than the first dataset.

4. The apparatus of claim 1, wherein the composite dataset comprises more of the first dataset than the second dataset.

5. The apparatus of claim 1, wherein the composite dataset comprises all of the second dataset.

6. The apparatus of claim 1, wherein the composite dataset comprises a most recent of the sensor data received from the analyte sensor.

7. The apparatus of claim 1, wherein each of the first data rate and the second data rate is based on a different fraction of the sampling rate of the analyte sensor.

8. The apparatus of claim 1, wherein the analyte sensor samples sensor data at a constant sampling rate.

9. The apparatus of claim 1, further comprising a first memory buffer having a first size configured to store the first dataset at the first data rate, and a second memory buffer having a second size configured to store the second dataset at the second data rate.

10. A method comprising:
    receiving sensor data from an analyte sensor;
    generating a composite dataset that comprises at least a first dataset and a second dataset based on the sensor data received from the analyte sensor, wherein the first dataset has a first data rate and the second dataset has a second data rate, and wherein each of the first data rate and second data rate is based on a different factor of a sampling rate of the analyte sensor; and
    estimating an analyte level based on the first dataset and the second dataset included in the composite dataset.

11. The method of claim 10, wherein the first data rate is greater than the second data rate.

12. The method of claim 10, wherein the composite dataset comprises more of the second dataset than the first dataset.

13. The method of claim 10, wherein the composite dataset comprises more of the first dataset than the second dataset.

14. The method of claim 10, wherein the composite dataset comprises all of the second dataset.

15. The method of claim 10, wherein the composite dataset comprises a most recent of the sensor data received from the analyte sensor.

16. The method of claim 10, wherein each of the first data rate and the second data rate is based on a different fraction of the sampling rate of the analyte sensor.

17. The method of claim 10, wherein the analyte sensor samples sensor data at a constant sampling rate.

18. The method of claim 10, wherein a first memory buffer having a first size is configured to store the first dataset at the first data rate, and wherein a second memory buffer having a second size is configured to store the second dataset at the second data rate.

* * * * *